(12) United States Patent
Maršič et al.

(10) Patent No.: US 7,524,871 B2
(45) Date of Patent: Apr. 28, 2009

(54) THROMBIN INHIBITORS

(75) Inventors: Lucija Peterlin Maršič, Medvode (SI);
Danijel Kikelj, Ljubljana (SI); Andreja Jurca, Žiri (SI); Petra Marinko, Ljubljana (SI); Alenka Trampuš Bakija, Ljubljana (SI); Mojca Stegnar, Ljubljana (SI); Dejan Delovič, Ljubljana (SI); Andrej Prezelj, Ljubljana (SI); Slavko Pečar, Radomlje (SI)

(73) Assignees: University of Ljubljana, Faculty of Pharmacy, Ljubljana (SI); Lek Pharmaceutical d.d., Ljubljana (SI)

( * ) Notice: Subject to any disclaimer, the term of this patent is extended or adjusted under 35 U.S.C. 154(b) by 550 days.

(21) Appl. No.: 10/497,328

(22) PCT Filed: Dec. 3, 2002

(86) PCT No.: PCT/IB02/05079

§ 371 (c)(1),
(2), (4) Date: Mar. 7, 2005

(87) PCT Pub. No.: WO03/048155

PCT Pub. Date: Jun. 12, 2003

(65) Prior Publication Data

US 2005/0165034 A1    Jul. 28, 2005

(30) Foreign Application Priority Data

Dec. 4, 2001    (SI) .............................. P-200100309

(51) Int. Cl.
*A61K 31/4439* (2006.01)
*C07D 401/12* (2006.01)
(52) U.S. Cl. ................................ 514/339; 546/275.7
(58) Field of Classification Search .............. 546/275.7; 514/339
See application file for complete search history.

(56) References Cited

U.S. PATENT DOCUMENTS 5,668,289 A    9/1997    Sanderson et al. .......... 546/293

FOREIGN PATENT DOCUMENTS

| WO | WO 97/01338 | 1/1997 |
| WO | WO 97/30708 | 8/1997 |
| WO | WO 97/46207 | 12/1997 |
| WO | WO 98/42342 | 10/1998 |
| WO | WO 99/61442 | 12/1999 |
| WO | WO 01/04117 | 1/2001 |
| WO | WO 01/79195 | 10/2001 |
| WO | WO 01/79262 | 10/2001 |

OTHER PUBLICATIONS

Gangjee, Zaveri, Queener and Kisliuk, "Synthesis and Biological Activities of Tetrahydroquinazoline Analogs", *J Heterocyclic Chem*, vol. 32, pp. 243-247 (1995).
Das and Kimball, "Thrombin Active Site Inhibitors", *Bioorg Med Chem*, vol. 3, No. 8, pp. 999-1007 (1995).
Kimball, "Thrombin Active Site Inhibitors", *Curr Pharm Des*, vol. 1, No. 4, pp. 441-468 (1995).
Menear, "Progress Towards the Discovery of Orally Active Thrombin Inhibitors", *Curr Med Chem*, vol. 5, No. 6, pp. 457-468 (1998).
Sanderson and Naylor-Olsen, "Thrombin Inhibitor Design", *Curr Med Chem*, vol. 5, No. 4, pp. 289-304 (1998).
Sanderson, "Small, Noncovalent Serine Protease Inhibitors", *Med Res Rev*, vol. 19, No. 2, pp. 179-197 (1999).
Tucker et al., "Design and Synthesis of a Series of Potent and Orally Bioavailable Noncovalent Thrombin Inhibitors That Utilize Nonbasic Groups in the P1 Position", *J Med Chem*, vol. 41, No. 17, pp. 3210-3219 (1998).
Edward J. Modest, et al., "2,4-Diaminopyrimidines from Dicyandiamide. III. Reaction with Monocyclic Ketones". J. Org. Chem. vol. 30, pp. 1837-1840 (1965).
Abdel-Magid et al., "Reductive Amination of Aldehydes and Ketones with Sodium Triacetoxyborohydride. Studies on Direct and Indirect Reductive Amination Procedures", *J Org Chem*, vol. 61, No. 11, pp. 3849-3862 (1996).
Bach et al., "Bicyclic and Tricyclic Ergoline Partial Structures. Rigid 3-(2-Aminoethyl)pyrroles and 3- and 4-(2-Aminoethyl)pyrazoles as Dopamine Agonists", *J Med Chem*, vol. 23, No. 5, pp. 481-491 (1980).
Breznik and Pečar, "Trombinski Inhibitorji", *Farm Vestn*, vol. 48, pp. 545-560 (1997).

*Primary Examiner*—Patricia L Morris
(74) *Attorney, Agent, or Firm*—Luekeka, Neely & Graham, P.C.

(57) ABSTRACT

Novel thrombin inhibitors of the formula I (I) and pharmaceutically acceptable salts thereof are described wherein the substituents in the description have the specific meanings. The compounds are useful as thrombin inhibitors.

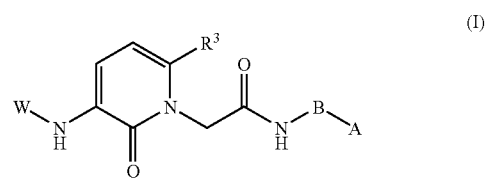

(I)

5 Claims, No Drawings

THROMBIN INHIBITORS

The invention belongs to the field of pharmaceutical industry and relates to novel heterocyclic derivatives of tripeptides and tripeptide mimetics, methods for their preparation and pharmaceutical compositions containing them.

Heterocyclic derivatives of tripeptides and tripeptide mimetics are inhibitors of thrombin and other serine proteases which play a role in blood coagulation and which have the anticoagulant activity. Nowadays, heparins and coumarins predominantly used for inhibition of coagulation in vivo have a number of untoward and unexpected effects. There is, therefore, a constant need for new substances with anticoagulant activity.

Serine protease thrombin is a key enzyme in the processes of blood coagulation and thus in the development of thrombosis. Its principal action is to convert soluble fibrinogen into insoluble fibrin which forms a mechanical matrix of the blood clot. In addition, it mechanically strengthens the clot by activating factor XII which covalently links fibrin monomers and stimulates platelet aggregation. By a positive feedback mechanism via activation of factors V and VIII the thrombin concentration at the site of injury is increased. With the above role played in hemostasis, thrombin has become a target molecule for the development of new anticoagulants (Sanderson P. E. J., Naylor-Olsen A. M. *Curr. Med. Chem.* 1998, 5, 289-304.; Menear K. *Curr. Med. Chem.* 1998, 5, 457-468.; Breznik M., Pečar S. *Farm. vestn.* 1997, 48, 545-560; Sanderson P. E. J. *Med. Res. Rev.* 1999, 19, 179-197). The active site of thrombin with the characteristic catalytic triad (Asp 189, His 57, Ser 195) can be divided into three binding areas: S1 pocket giving the enzyme specificity for the basic part of the inhibitor molecule P1, S2 hydrophobic area which prevents access of the inhibitors and the substrate to the active site, and a larger S3 hydrophobic area (Bode W., Mayr I., Baumann U. et al. *EMBO Journal* 1988, 8, 3467-3475).

Based on the knowledge of the crystalline structure of thrombin, a number of low molecular weight inhibitors have been developed which act at the thrombin active site. An ideal thrombin inhibitor should have good bioavailability, long half-life and be suitable for oral administration. Achievement of these aims is limited either by a basic guanidine or amidine group, present in P1 moiety of many known thrombin inhibitors or by a reactive electrophilic group, present in electrophilic thrombin inhibitors, for example—in efegatran-and PPACK. An important criterion in designing thrombin inhibitors is also the selectivity to other serine proteases, such as trypsin, factor Xa, urokinase, tissue plasminogen activator and plasmin (Kimball S. D. *Current Pharmaceutical Design* 1995, 1, 441-468.; Das J., Kimball S. D. *Bioorg. Med. Chem.* 1995, 3, 999-1007).

Low molecular weight inhibitors of the thrombin active site mimic a tripeptide sequence D-Phe-Pro-Arg which binds to the thrombin active site. The first phase in the development were irreversible inhibitors which covalently react with Ser 195 at the active site. PPACK is a prototype of this type of inhibitor having a high reactivity. Argatroban is the first highly effective and selective reversible inhibitor available on the market. A large number of structurally different, active reversible inhibitors with hydrophilic basic groups having low bioavailability after oral administration have been synthesised to date (Menear K. *Curr. Med. Chem.* 1998, 5, 457-468).

By extensive modification of the P1 part of thrombin inhibitors, primarily by substituting basic guanidine or amidine groups with neutral or weakly basic groups, their bioavailability can be increased. Larger groups in this part of the molecule lead to higher selectivity of the inhibitors for thrombin as, compared to the majority of other serine proteases, thrombin has relatively large S1 pocket. Selectivity of thrombin inhibitors is generally estimated regarding their ability for inhibition of trypsin which by form and size of the active site is most closely related to thrombin and has a smaller S1 pocket. Modification of other parts of the molecule (P2 and P3), especially substitution of the ester and amide bonds, may further increase the stability of thrombin inhibitors in the body. Such thrombin inhibitors are less sensitive to nonspecific proteases and hydrolysis and consequently their half-life increases (Menear K. *Curr. Med. Chem.* 1998, 5, 457-468.; Tucker T. J., Brady S. F., Lumma W. C. et al. *J. Med. Chem.* 1998, 41, 3210-3219).

An object of the invention is, therefore, to provide novel compounds suitable for the use in therapy or in manufacturing novel medicaments.

This object is achieved for example by the combination of the features defined in each of the claims.

According to one aspect of the invention the object is achieved for example by the novel compounds of the general formula I

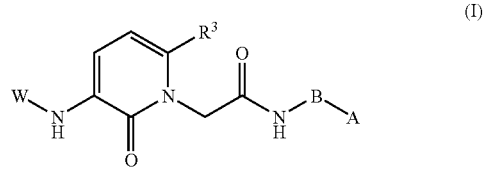

wherein:
W is
  $R^1$,
  $R^1OCO$,
  $R^1CO$,
  $R^1SO_2$,
  $(R^1(CH_2)_n)_mNH_qCO$, where n is 0, 1, 2, 3 or 4,
    where m is 1 or 2 and
    where q is 0 or 1, with the proviso
      that where n is 1, 2, 3 or 4, q is 1 and m is 1,
      and where n is 0, m is 1 or 2 and q is 0 or 1,
      and where n is 0, m is 2 and q is 0, and
    wherein $R^1$ can be the same or different;
$R^1$ is
  $R^2(CH_2)_n$, where n is 0, 1, 2, 3 or 4,
  $(R^2)(OR^2)CH(CH_2)_p$, where p is 1, 2, 3 or 4,
  $(R^2)_2CH(CH_2)_n$, where n is 0, 1, 2, 3 or 4, and $R^2$ can be the same or different, and
  $R^2O(CH_2)_p$, where p is 1, 2, 3 or 4;
$R^2$ is
  hydrogen,
  phenyl, unsubstituted or substituted with one or more $C_{1-4}$ linear or branched alkyl, $C_{1-4}$ linear or branched alkoxy, halogen, trifluoromethyl, hydroxy, $COOR^4$, $CONHR^4$, nitro, $NHR^4$ or $NR^4R^4$ group(s),
  naphthyl,
  biphenyl,
  5- to 7-membered monocyclic or 9- to 10-membered bicyclic heterocyclic ring system which can be substituted or unsubstituted and which, in addition to carbon atoms, contains up to 3 heteroatoms selected from N, O and S,
  $COOR^4$,
  $C_{1-4}$ linear or branched alkyl,
  $C_{3-7}$ cycloalkyl, or
  $C_{7-12}$ bicycloalkyl;

R⁴ is
  hydrogen, or
  $C_{1-4}$ linear or branched alkyl;
R³ is
  hydrogen,
  $C_{1-4}$ linear or branched alkyl,
  $C_{3-7}$ cycloalkyl, or
  trifluoromethyl group;
B is
  $(CH_2)_k$, where k is 0 or 1; and
A is chosen from one of the following radicals:

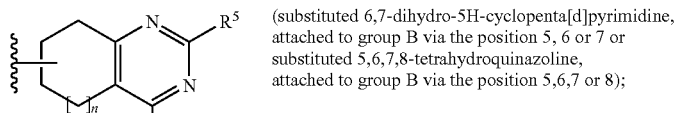

(substituted 6,7-dihydro-5H-cyclopenta[d]pyrimidine, attached to group B via the position 5, 6 or 7 or substituted 5,6,7,8-tetrahydroquinazoline, attached to group B via the position 5,6,7 or 8);

n = 0 or 1

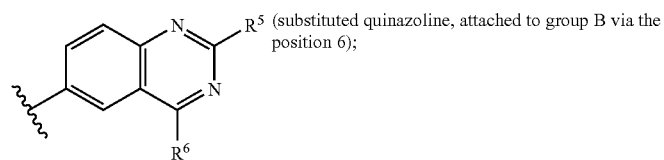

(substituted quinazoline, attached to group B via the position 6);

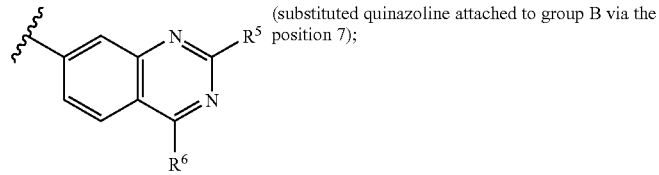

(substituted quinazoline attached to group B via the position 7);

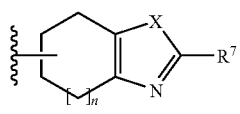

n = 0, 1
where X is S, NH or O (substituted 1,4,5,6-tetrahydrocyclopenta[d]-imidazole, 5,6-dihydro-4H-cyclopenta[d]-[1,3]-thiazole, 5,6-dihydro-4H-cyclopenta[d][1,3]-oxazole, attached to group B via the position 4, 5 or 6 or substituted 4,5,6,7-tetrahydro-1,3-benzothiazole, 4,5,6,7-tetrahydro-1H-benzimidazole or 4,5,6,7-tetrahydro-1,3-benzoxazole, attached to group B via the position 4, 5, 6 or 7);

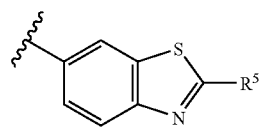

(substituted 1,3-benzothiazole, attached to group B via the position 6):

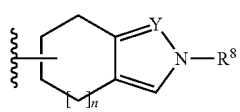

n = 0, 1
wherein Y is N or CH (substituted 2,4,5,6-tetrahydrocyclopenta[c]pyrrole, 2,4,5,6-tetrahydrocyclopenta[c]pyrazole, attached to group B via the position 4, 5 or 6 or substituted 4,5,6,7-tetrahydro-2H-indazole, 4,5,6,7-tetrahydro-2H-isoindole, attached to group B via the position 4, 5, 6 or 7);

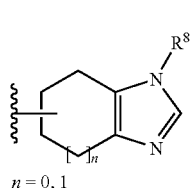

n = 0, 1

(substituted 5,6-dihydro-4H-cyclopenta[d]imidazole, attached to group B via the position 4, 5 or 6 or substituted 4,5,6,7-tetrahydro-1H-benzimidazole, attached to group B via the position 4, 5, 6 or 7);

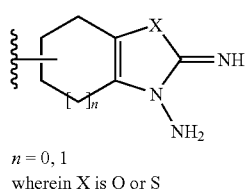

n = 0, 1
wherein X is O or S (substituted 2-imino-5,6-dihydro-4H-cyclopenta[d][1,3]-thiazol-3-ylamine, 2-imino-5,6-dihydro-4H-cyclopenta[d][1,3]-oxazol-3-ylamine attached to group B via the position 4, 5 or 6 or (substituted 2-imino-4,5,6,7-tetrahydro-1,3-benzothiazol-3(2H)-ylamine, substituted 2-imino-4,5,6,7-tetrahydro-1,3-benzoxazol-3(2H)-ylamine attached to group B via the position 4, 5, 6 or 7).

$R^5$ is hydrogen or $NH_2$;

$R^6$ is hydrogen or $NH_2$;

$R^7$ is hydrogen, $NH_2$ or $NHC(NH)NH_2$, and $R^8$ is hydrogen, $CH_3$, ethyl, propyl, cyclopropyl or $C(NH)NH_2$.

A further aspect of the invention is the use of the compounds of formula I according to the invention in therapy or for manufacturing novel medicaments for inhibiting thrombin and fibrin formation and for inhibiting thrombus formation in man and other mammals.

A further aspect of the invention is a pharmaceutical composition comprising a therapeutically effective amount of the compounds of the invention and the use of this pharmaceutical composition for inhibiting thrombin or inhibiting formation of fibrin in blood of man or mammals.

A further aspect of the invention is a process for the preparation of the novel compounds of formula I by condensation reaction.

The above and further aspects to achieve the object according to the invention together with the features and effects obtained will be more obvious from the embodiments described in the following.

The compounds of the present invention have one or more stereogenic centres whose absolute configuration can be R or S and can be present in the form of racemates, racemic mixtures, pure enantiomers, mixtures of diastereomers or pure diastereomers.

Preferred embodiments are compounds wherein W is $R^1$ or $R^1SO_2$ and wherein $R^1$ is $R^2(CH_2)_n$. Especially useful class of compounds is the embodiment wherein $R^3$ is $CH_3$.

In one exemplification of the invention, W is $R_1SO_2$, $R^3$ is $CH_3$, B is $CH_2$, and A is 4,5,6,7-tetrahydroindazole attached to group B via the position 5. Specific embodiments of this class include (note that the methyl group is conventionally indicated as a single bond attached to a ring):

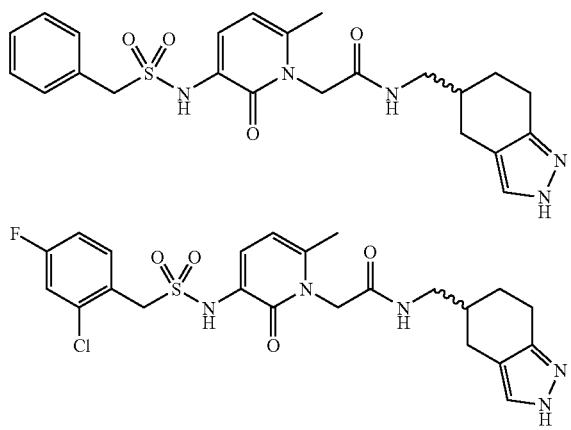

In another exemplification of the invention, W is $R^1SO_2$, B is $(CH_2)_k$ wherein k is 0 and A is 4,5,6,7-tetrahydro-1,3-benzothiazole attached to group B via the position 6.

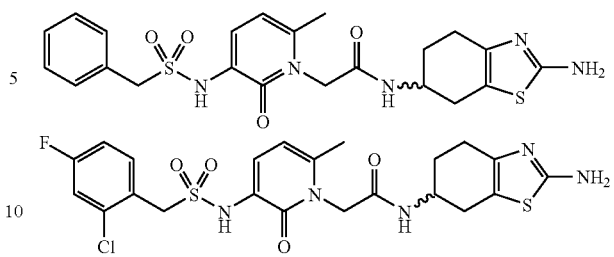

In a third exemplification of the invention, W is $R^1$, B is $(CH_2)_k$ wherein k is 0 and A is 4,5,6,7-tetrahydro-1,3-benzothiazole attached to group B via the position 6.

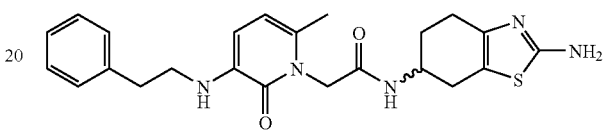

In a fourth exemplification of the invention, W is $R^1$, B is $CH_2$ and A is 4,5,6,7-tetrahydroindazole attached to group B via the position 5.

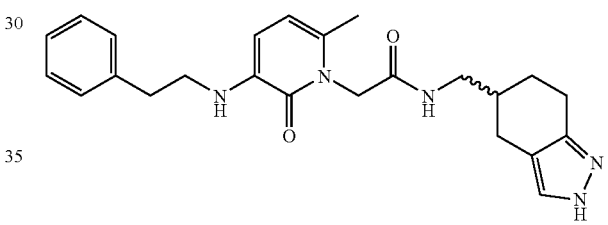

The invention also relates to the pharmaceutically acceptable salts of the compounds of formula I obtainable by treating the compounds I according to the invention with acids or bases in suitable organic solvents conventionally used in this technical field.

The pharmaceutically acceptable salts of the compounds of formula I (in the form of water- or oil-soluble or dispersible products) include the conventional non-toxic salts or the quaternary ammonium salts which are formed, e.g., from inorganic or organic acids or bases. Examples of such acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, hydrobromide, hydrochloride, hydroiodide, lactate, maleate, methanesulfonate, nicitinate, nitrate, oxalate, pamoate, 3-phenylpropionate, picrate, pivalate, propionate, pectinate, succinate, sulfate, tartrate, thiocyanate, tosylate, and audecanoate. Base salts include ammonium salts, alkali metal salts such as sodium and potassium salts, alkaline earth metal salts such as calcium and magnesium salts, N-methyl-D-glucamine and salts with amino acids such as arginine, lysine, and so forth. Also, the basic nitrogen-containing groups may be quaternized with such agents as lower alkyl halides, dialkylsulfates, and diamylsulfates, long chain halides, aralkyl halides and others.

The invention further provides the use of novel compounds of the formula I for manufacturing medicaments comprising therapeutically effective ingredients. The novel compounds are thrombin inhibitors having improved activity, good bioavailability, long half-life and are capable of being orally administered. They inhibit thrombin and formation of fibrin. In particular, the compounds of the invention have a good selectivity of the thrombin inhibiting activity with respect to trypsin inhibition.

They are useful in the treatment or prevention of a variety of thrombosis forms: (i) venous thromboembolism due to formation of a thrombus within a vein (venous thrombosis) associated with acquired (prolonged bedrest, surgery, injury, malignancy, pregnancy and postpartum states) or inherited (deficiency of natural coagulation inhibitors) risk factors, obstruction or occlusion of a lung artery by a detached thrombus (pulmonary embolism), (ii) cardiogenic thromboembolism due to formation of a thrombus in the heart associated with cardiac arrhythmia, heart valve defect, prosthetic heart valves or heart disease, embolism of peripheral arteries caused by a detached thrombus, most commonly in the brain (ischemic stroke), (iii) arterial thrombosis due to underlying atherosclerotic processes in the arteries which obstructs or occludes an artery and causes myocardial ischemia (angina pectoris, acute coronary syndrome) or myocardial infarction, obstructs or occludes a peripheral artery (ischemic peripheral artery disease) and obstructs or occludes the artery after the procedure on the blood vessel (reocclusion or restenosis after transluminal coronary angioplasty, reocclusion or restenosis after percutaneous transluminal angioplasty of peripheral arteries) and (iv) in the number of states (e.g., in complications in pregnancy, in metastasing malignant diseases, after extensive injuries, in bacterial sepsis) when thrombogenic activation causes widespread formation of thrombi within the vascular system (disseminated intravascular coagulation).

The compounds of the present invention may be also used as an adjunct therapy in conjunction with thrombolytic therapy in recent myocardial infarction, in combination with aspirin in patients with unstable angina pectoris designed to undergo percutaneous transluminal angioplasty and in the treatment of patients with thrombosis and with heparin-induced thrombocytopenia.

The compounds of the present invention may further be used for the prevention of blood coagulation which is in contact with nonbiological surfaces (vascular prosthesis, vascular stents, prosthetic heart valves, extracorporeal circulation systems, hemodialysis) and in vitro to prevent coagulation in biological samples for testing or storage.

The pharmaceutical compositions comprising the compounds of the formula I according to the present invention may be formulated as injectable or oral formulations. In addition to the active ingredient they preferably contain different standard additives depending on the use. The pharmaceutical compositions can be prepared according to the standard procedures.

The preparation may be formulated in such a manner as to permit controlled and sustained release of the active ingredient. Dosage, frequency and mode of administration depend on a variety of factors, they also depend on individual active ingredient and its pharmacokinetic parameters and on patient's condition.

Embodiments for the processes for the preparation of compounds of general formula I according to the invention are described in the following.

The starting heterocyclic compounds are prepared as depicted in Schemes 1, 11 and III or according to the methods described in the literature.

2,4,6-Triamino-5,6,7,8-tetrahydroquinazoline (3), 2,6-diamino-4,5,6,7-tetrahydro-1,3-benzothiazole (4), 2,6-diamino-5,6,7,8-tetrahydroquinazoline (5) and 5-amino-4,5,6,7-tetrahydro-2H-indazole (6) are prepared according to the procedures described in SI patent application P-200000111 and depicted in Scheme I. 3-Amino-2-imino-4,5,6,7-tetrahydro-1,3-benzothiazol-6(2H)-ylamine is prepared from N-(4-oxocyclohexyl)acetamide (1) by bromination, cyclization with thiosemicarbazide and subsequent acid hydrolysis. 2-Methyl-4,5,6,7-tetrahydro-2H-indazol-5-ylamine (7) is prepared from enaminoketone (2) by cyclization with N-methylhydrazine and subsequent acid hydrolysis (Scheme I). 4,5,6,7-Tetrahydro-2H-isoindol-5-amine is prepared by alkaline catalyzed reaction of enaminoketone (2) with glycine to the corresponding—K salt which after addition of acetanhydride is cyclized, decarboxylated and the compound formed is acetylated to suitable diamide which by subsequent basic hydrolysis is converted to the corresponding amine (Bach N. J., Kornfeld E. C., Jones N. D. et al. *J. Med. Chem.* 1980, 23, 481).

SCHEME I

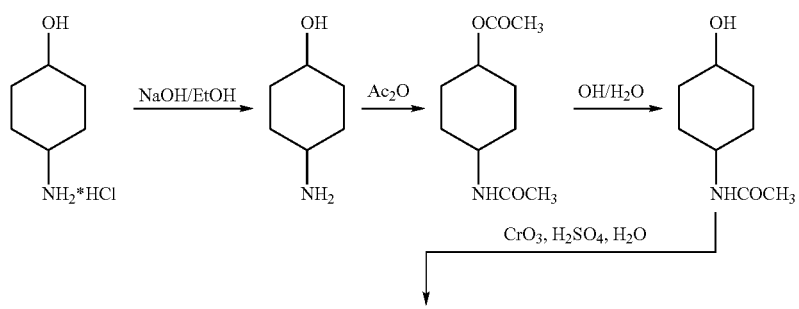

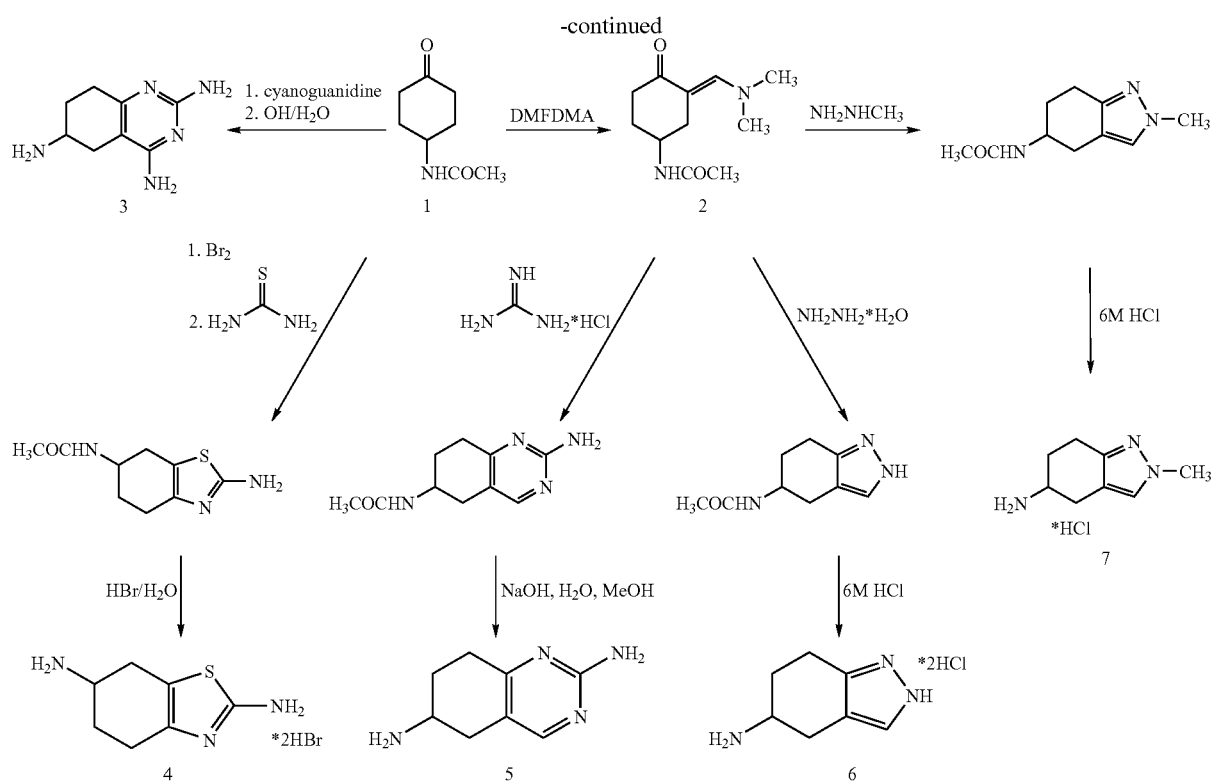

2,4,5-Triamino-5,6,7,8-tetrahydroquinazoline, 2,5-diamino-5,6,7,8-tetrahydroquinazoline, 4-amino-4,5,6,7-tetrahydro-2H-indazole, 4-amino-4,5,6,7-tetrahydro-2H-isoindole and 2-methyl-4,5,6,7-tetrahydro-2H-indazol-4-ylamine are prepared from 1,3-cyclohexanedione and a suitable reagent for cyclization analogously to the procedures described in the articles: Bach N. J., Kornfeld E. C., Jones N. D. et al. *J. Med. Chem.* 1980, 23, 481.; Modest E. J., Chatterjee S., Protopapa H. K. *J. Am. Chem. Soc.* 1965, 87, 1837.; Gangjee A., Zaveri N., Queener S. F. et al. *J. Heterocyclic Chem,* 1995, 32, 243 and subsequent conversion of the keto group into the amino group, for example by reductive amination (Abdel-Magid A. F., Carson K. G., Harris B. D. et al. *J. Org. Chem.* 1996, 61, 3849).

2,7-Diamino-4,5,6,7-tetrahydro-1,3-benzothiazole, 2,4-diamino-4,5,6,7-tetrahydro-1,3-benzothiazole, 2,4,8-triamino-5,6,7,8-tetrahydroquinazoline, 2,8-diamino-5,6,7,8-tetrahydroquinazoline, 7-amino-4,5,6,7-tetrahydro-2H-indazole, 7-amino-4,5,6,7-tetrahydro-2H-isoindole, 2,6-diamino-1,3-benzothiazole, 2,5-diamino-4,5,6,7-tetrahydro-1H-benzimidazole, 2,4-diamino-4,5,6,7-tetrahydro-1H-benzimidazole, 2,6-diamino-4,5,6,7-tetrahydro-1,3-benzoxazole, and 2,4-diamino-4,5,6,7-tetrahydro-1,3-benzoxazole are prepared according to the procedures described in SI patent application no. P-200000111.

Starting from cyclopentane-1,3-dione, cyclopentan-1,3-dione monoethylene acetal and N-(3-oxocyclopentyl)acetamide according to analogous procedures as described in SI patent application no. P-200000111, the amino derivatives of 6,7-dihydro-5 H-cyclopenta[d]pyrimidine, 1,4,5,6-tetrahydrocyclopenta[d]imidazole, 5,6-dihydro-4 H-cyclopenta[d][1,3]thiazole, 5,6-dihydro-4H-cyclopenta[d][1,3]oxazole, 2,4,5,6-tetrahydrocyclopenta[c]pyrrole, 2,4,5,6-tetrahydrocyclopenta-[c]pyrazole and 5,6-dihydro-4H-cyclopenta[d]imidazole are prepared.

As depicted in Scheme II and described in SI patent application no. P-200000111, 6-(aminomethyl)-5,6,7,8-tetrahydro-2-quinazolinamine (10) (Peterlin-Masič, L.; Kikelj, D. *Tetrahedron Lett.* 2000, 41, 5589), 4,5,6,7-tetrahydro-2H-isoindol-5-ylmethanamine (12), 4,5,6,7-tetrahydro-2H-indazol-5-ylmethanamine (11) (Peterlin-Masič, L.; Kikelj, D. *Tetrahedron Lett.* 2000, 41, 5589), 6-(aminomethyl)-4,5,6,7-tetrahydro-1,3-benzothiazol-2-amine (15) and 6-(aminomethyl)-5,6,7,8-tetrahydro-2,4-quinazolinediamine (17) are prepared. 2-Methyl-4,5,6,7-tetrahydro-2H-indazole-5-yl)methanamine (13) is prepared from enaminoketone (9) by cyclization with N-metylhydrazine and subsequent acid hydrolysis (Scheme II). N-[6-(Aminomethyl)-4,5,6,7-tetrahydro-1,3-benzothiazol-2-yl]guanidine (14) is prepared from ketone (8) by cyclization with amidinothiourea and subsequent acid hydrolysis. According to the analogous procedure 4,5,6,7-tetrahydro-1 H-benzimidazole-6-ylmethanamine (16) is prepared from (8) and formamidine hydrochloride (Scheme II). 3-Amino-2-imino-4,5,6,7-tetrahydro-1,3-benzothiazol-6(2 H)-ylmethylamine is prepared from N-[(4-oxocyclohexyl)methyl]acetamide (8) by bromination, cyclization with thiosemicarbazide and subsequent acid hydrolysis.

4-(Aminomethyl)-4,5,6,7-tetrahydro-1,3-benzothiazol-2-amine, 4,5,6,7-tetrahydro-2H-isoindol-7-ylmethanamine, 4,5,6,7-tetrahydro-2H-indazol-7-ylmethanamine, 8-(aminomethyl)-5,6,7,8-tetrahydro-2,4-quinazolinediamine and 8-(aminomethyl)-5,6,7,8-tetrahydro-2-quinazolinamine are prepared according to the procedures described in SI patent application no. P-200000111.

SCHEME II

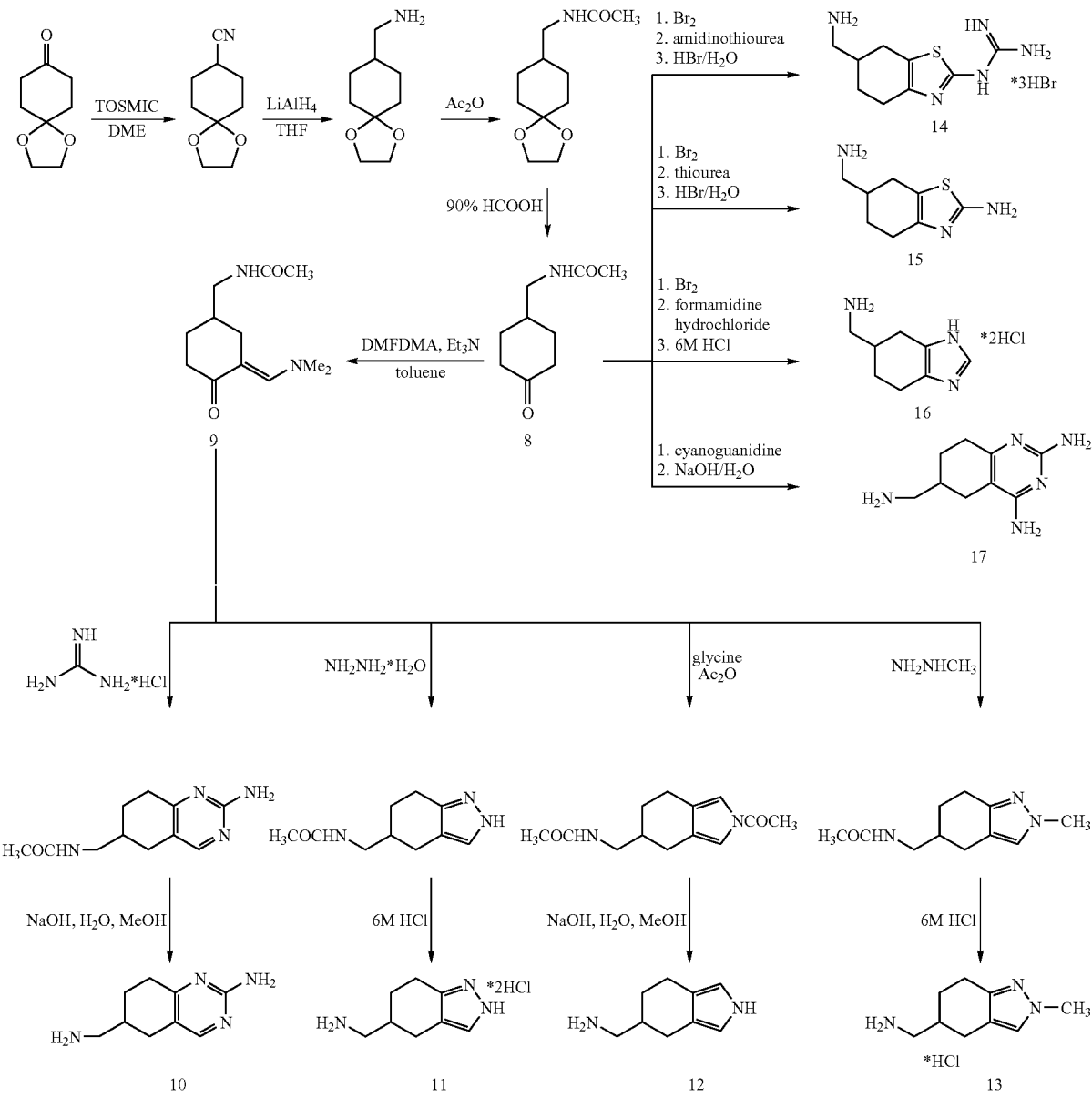

Starting from cyclopentane-1,3-dione, cyclopentane-1,3-dione monoethylene acetal and N-(3-oxocyclopentyl)acetamide according to the analogous procedures as described in SI patent application no. P-200000111 and depicted in Scheme II, aminomethyl derivatives of 6,7-dihydro-5H-cyclopenta[d]pyrimidine, 1,4,5,6-tetrahydrocyclopenta[d]imidazole, 5,6-dihydro-4H-cyclopenta-[d][1,3]thiazole, 5,6-dihydro-4H-cyclopenta[c][1,3]oxazole, 2,4,5,6-tetrahydrocyclopenta[c]pyrrole, 2,4,5,6-tetrahydrocyclopenta[c]pyrazole and 5,6-dihydro-4H-cyclopenta[d]imidazole are prepared.

6-(Aminomethyl)-4-quinazolinamine, 7-(aminomethyl)-4-quinazolinamine, 6-(aminomethyl)-2-quinazolinamine, 7-(aminomethyl)-2-quinazolinamine, 6-(aminomethyl)-2,4-quinazolinediamine and 7-(aminomethyl)-2,4-quinazolinediamine are prepared from 6-(bromomethyl)4-chloroquinazoline, 7-(bromomethyl)-4-chloroquinazoline, 6-(bromomethyl)-2-chloroquinazoline, 7-(bromomethyl)-2-chloroquinazoline, 6-(bromomethyl)-2,4-dichloroquinazoline or 7-(bromomethyl)-2,4-dichloroquinazoline and ammonia in polar organic solvents at increased pressure and elevated temperature. The above 6-bromomethyl- and 7-(bromomethyl)chloroquinazolines are prepared by bromination of 6-methyl-4-chloroquinazoline, 6-methyl-2-chloroquinazoline, 7-methyl-4-chloroquinazoline, 7-methyl-2-chloroquinazoline, 6-methyl-2,4-dichloroquinazoline and 7-methyl-2,4-dichloroquinazoline according to the procedure as, for example, described for the preparation of 6-bromomethyl-4-chloroquinazioline in EP 566226 and in SI patent application no. P-200000111.

tert-Butyl {6-[(acetylamino)methyl]-4,5,6,7-tetrahydro-1 H-benzimidazol-1-yl}[(tert-butoxy-carbonyl)amino]methylidenecarbamate (18) and tert-butyl{6-[(acetylamino)methyl]-4,5,6,7-tetrahydro-1H-benzimidazol-1-yl}[(tert-butoxycarbonyl)amino]methylidenecarmabate (19) are prepared as disclosed in Scheme III from suitable tetrahydroindazole and tetrahydrobenzimidazole-derivative, respectively with N,N-di-(Boc)-S-methylisothiourea according to the analogous procedure as described in the article Nicholau K. C. et al. *Bioorg. Med. Chem. Lett.* 1998, 6, 1185 and subsequent alkaline hydrolysis of the acetamide group.

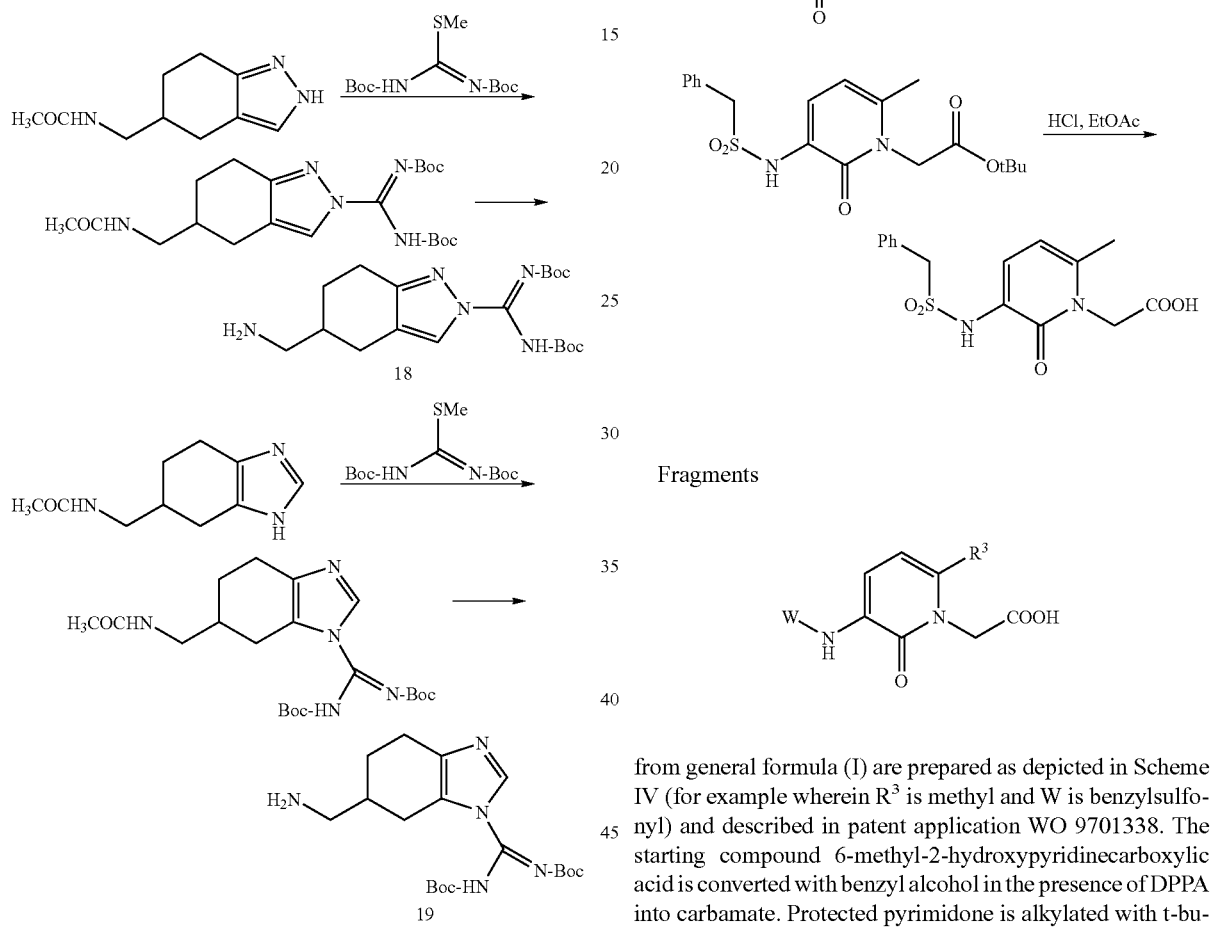

Fragments

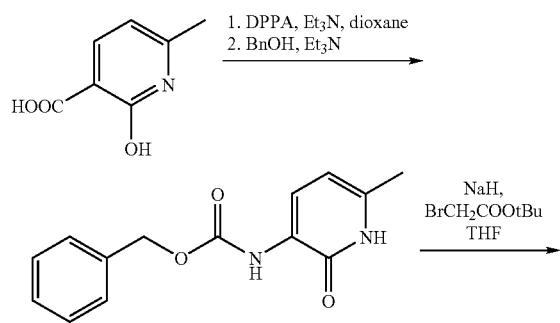

from general formula (I) are prepared as depicted in Scheme IV (for example wherein $R^3$ is methyl and W is benzylsulfonyl) and described in patent application WO 9701338. The starting compound 6-methyl-2-hydroxypyridinecarboxylic acid is converted with benzyl alcohol in the presence of DPPA into carbamate. Protected pyrimidone is alkylated with t-butylbromoacetate in the presence of a base. Then the Cbz group is removed by catalytic hydrogenation. The obtained amine reacts with suitable reagents, in our example with benzylsulfonyl chloride in the presence of pyridine. Finally, the Boc protective group is removed under the acidic conditions.

Using suitably substituted starting compounds and reagents in individual reaction steps, the compounds with suitable W and $R^3$ groups can be analogously prepared. For example, pyridinone substituted at position 6 with ethyl, isopropyl, cyclopropyl or similar group, can be used as a starting compound to obtain compounds with different $R^3$ substituents. Compounds with different W fragments, wherein W is $R^1$, $R^1OCO$, $R^1CO$, $R^1SO_2$ or $(R^1(CH_2)_n)_mNCO$, can be prepared by using suitable reagents for alkylation, acylation, sulfonation and carbamoylation such as, for example, alkyl halides, alkoxycarbonyl halides, acyl halides or alkyl isocynates in the second step of synthesis.

SCHEME V

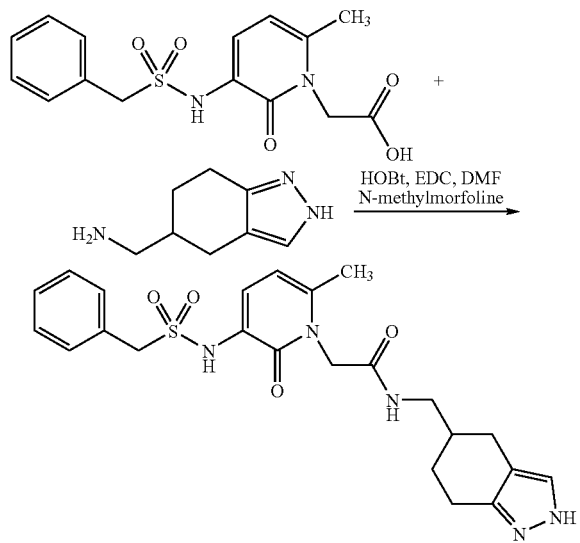

Compounds of general formula (I) are prepared by condensation of fragment

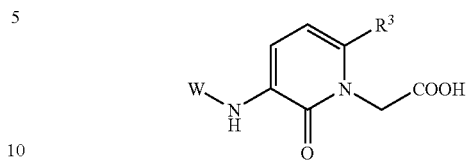

(Scheme IV) with fragment A-B-NH$_2$ (Schemes I-III) as presented in Schemes V and VI. For condensation, conventional reagents may be used for formation of the peptide bond as, for example, dicyclohexyl carbodiimide, EDC, HOBt, DPPA or chloroformates, etc. (see, for example, Bodanszky M., Bodanszky A. *The Practice of Peptide Synthesis*, Springer, Berlin, 1994). For the removal of protecting groups, as presented for example in Scheme VI, generally known procedures can be used as described, for examples, in the books: (Green T. W. *Protecive groups in organic synthesis*, John Wiley § Sons, New York, 1980; Kocienski P. J. *Protecting groups*, Thieme Verlag, Stuttgart, 1994).

SCHEME VI

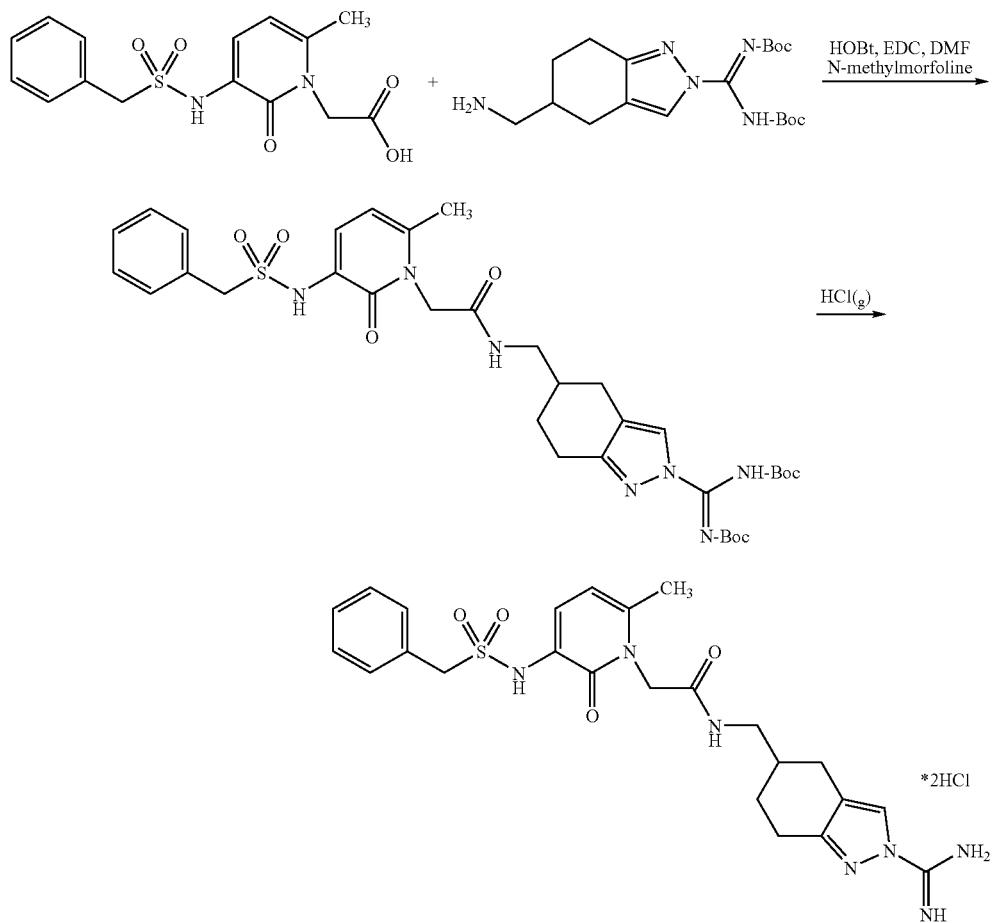

Pharmaceutically acceptable salts of the compounds of formula I are prepared by treating the compounds I with acids or bases in suitable organic solvents conventionally used in this technical field.

Biological Tests

I. Enzyme Assay for Determination of the Activity of Thrombin Inhibitors

1. Principle

Thrombin cleaves amide bonds in a synthetic chromogenic substrate whereby brown coloured p-nitroaniline (p-NA) is released. The amount of p-NA produced is directly proportionate to the absorbance measured at a wavelength of 405 nm using a spectrophotometer. When thrombin inhibitor is added, the amidolytic activity of the enzyme decreases. The potency of the inhibitor is expressed by the inhibition constant ($K_i$).

2. Reagents

Thrombin (human thrombin, 308 NIH units, Sigma): the contents of the vial are dissolved in distilled water to give a stock solution of 20 NIH units/ml. The stock solution is pipetted into 0.5 mL aliquots and stored at −70° C. Immediately before use a working solution of thrombin of NIH units/mL activity is prepared with HBSA buffer. The final concentration of thrombin in a microtiter plate is 0.5 NIH units/mL.

Chromogenic substrate for thrombin (S-2238, Chromogenix, 25 mg). 1 mM substrate solution is prepared, pipetted into 0.5 mL aliquots and stored at −20° C. Before use, 160 and 80 µM substrate solutions of the substrate are prepared with distilled water. The final concentrations of the substrate in the reaction mixture are 40 and 20 µM ($K_m$=2.6 µM), respectively.

HBSA buffer, pH 7.5: 10 mM Hepes buffer (HEPES, Sigma), 150 mM NaCl and 0.1% (w/v) bovine serum albumin (98% bovine serum albumin, Sigma) are dissolved in bidistilled water. The pH is adjusted with 0.1 M NaOH solution.

Inhibitors are dissolved in DMSO to give a 10 mM stock solution. Working solutions (final concentrations within the range 10 to 100 µM) are prepared with distilled water. The highest concentration of DMSO in a microtiter plate does not exceed 3%.

3. Procedure

Measurements are carried out in the microtiter plate. 50 µL HBSA buffer, 50 µL inhibitor solution of different concentrations (for control 50 µL HBSA buffer) and 50 µL of thrombin solution are pipetted into the wells of a microtiter plate. The plate is incubated at a temperature of 25° C. for 15 minutes. After incubation 50 µL of the chromogenic substrate is added and the microtiter plate is placed in the spectrophotometer (Tecan, Sunrise). The absorbance increase at 405 nM is measured at 10-second intervals for a period of 15 minutes at a temperature of 25° C.

For determination of the inhibition constant ($K_i$) 40 and 20 µM substrate is used. Each measurement is carried out in triplicate and the result is the averaged value of three measurements.

4. Determination of the Inhibition Constant ($K_i$)

$K_i$ is determined according to the principle, described by Cheng and Prusoff (Biochem Pharmacol, 1973, 22, 3099). Initial velocities of the reaction in the presence and absence of the inhibitor are measured. The change in the absorbance in the time unit (v) is calculated from the initial, linear part of the reaction. For competitive inhibitors it holds that $$\frac{v_i}{v_0} = \frac{K_m + S}{K_m \cdot (1 + (I/K_i)) + S}$$

and it follows that $$K_i = \frac{I}{((S/K_m) + 1) \cdot ((v_0/v_i) - 1)}$$

I=inhibitor concentration, S=substrate concentration, $K_m$=Michaelis constant, $v_o$=initial velocity of the reaction in the absence of inhibitor, $v_i$=initial velocity of the reaction in the presence of inhibitor.

Measurements are carried out with two concentrations of the inhibitor and two concentrations of the substrate. For each combination of the used concentrations of the substrate and the inhibitor, $K_i$ is calculated and the result is their averaged value.

II. Determination of Selectivity of the Inhibitor Activity Against Thrombin with Respect to Trypsin Inhibition 1. Principle Because thrombin and trypsin are closely related with respect to the specificity against the substrate due to comparable structure of the active site, the selectivity of inhibitory activity against thrombin is determined with respect to trypsin inhibition which is a nonspecific serine protease. The inhibitory activity against thrombin is determined as described above. Trypsin inhibition is measured in the same manner as in determination of inhibitory activity for thrombin except that a different chromogenic substrate is used. For both enzymes $K_i$ is calculated. Selectivity of the inhibitor is expressed as a ratio of $K_i$ for trypsin to $K_i$ for thrombin.

2. Reagents

Trypsin (bovine, 6000 BAEE Units/mg protein, Sigma): A stock solution of trypsin with the activity of 300 U/mL is prepared, pipetted into 0.2 mL aliquots and stored at −70° C. Immediately before use, the stock solution is thawed and a working solution of 4 mU/mL is prepared with HBSA buffer. The final trypsin activity in a microtiter plate is 1 mU/mL.

Chromogenic substrate for trypsin (S-2222, Chromogenix, 25 mg): 2 mM substrate solution is prepared, pipetted into 0.3 mL aliquots and stored at −20° C. Before use the stock solution is thawed and 400 and 200 µM substrate solutions are prepared The final concentrations of the substrate in the reaction mixture are 100 and 50 µM. ($K_m$=25 µM).

HBSA buffer, pH 7.5: 10 mM Hepes buffer (HEPES, Sigma), 150 mM NaCl and 0.1% (w/v) bovine serum albumin (98% bovine serum albumin, Sigma) are dissolved in bidistilled water. The pH is adjusted with 0.1 M NaOH solution.

Inhibitors are dissolved in DMSO to give a 10 mM stock solution. Working solutions (final concentrations in the range from 10 to 600 µM) are prepared with distilled water. The highest concentration of DMSO in a microtiter plate does not exceed 10%.

For determination of $K_i$ 100 and 50 µM substrate is used. Each measurement is carried out in triplicate and the result is the averaged value of three measurements.

3. Procedure

The procedure is the same as the procedure described for determination of the inhibitory activity against thrombin. The concentrations of the reagents described for determination of the inhibitory activity with respect to trypsin are used.

4. Determination of the Inhibition Constant ($K_i$)

It is determined in the same manner as determination of $K_i$ for thrombin.

5. Determination of the Selectivity $K_i$ for thrombin and $K_i$ for trypsin are determined. The selectivity is defined as the ratio:

$$\text{selectivity} = \frac{K_i(\text{trypsin})}{K_i(\text{thrombin})}$$

Abbreviations

| ABBREVIATIONS | |
| --- | --- |
| Boc | tert-butyloxycarbonyl |
| Cbz | Benzyloxycarbonyl |
| HOBt | 1-hydroxy benzotriazole hydrate |
| EDC | N'-(3-dimethylaminopropyl)-N-ethyl-carnodiimide hydrochloride |
| DPPA | Diphenylphosphorylazide |
| DMF | N,N-dimethylformamide |
| Et₃N | Triethylamine |
| EtOH | Ethanol |
| MeOH | Methanol |
| THF | Tetrahydrofuran |
| EtOAc | Ethylacetate |

The invention is illustrated but in no way limited by the following examples:

EXAMPLE 1

Synthesis of (±)-2-[3-[(benzylsulfonyl)amino]-6-methyl-2-oxo-1(2H)-pyridinyl]-N-[(4,5,6,7-tetrahydro-2H-indazole-5-yl]acetamide

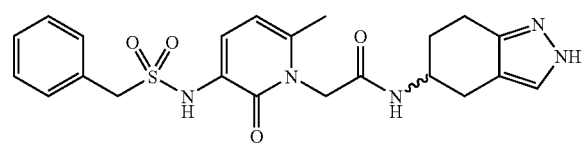

Step 1: Synthesis of 3-benzyloxycarbonylamino-6-methyl-2-pyridinone

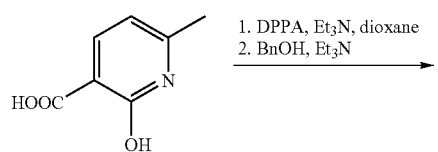

1. DPPA, Et₃N, dioxane
2. BnOH, Et₃N

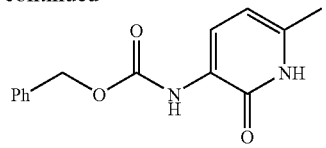

DPPA (8.5 mL, 39.2 mmol) was added to a stirred mixture of 2-hydroxy-6-methylpyridine-3-carboxylic acid (6.00 g, 39.2 mmol) and triethylamine (5.5 mL, 39.2 mmol) in anhydrous dioxane (72 mL) and the resulting solution was refluxed for 16 hours. Triethylamine (5.5 mL, 39.2 mmol) and benzyl alcohol (4.2 mL, 36.8 mmol) were added and the solution was refluxed for further 24 hours. The reaction mixture was concentrated in vacuo. To the residue were added dichloromethane (130 mL) and saturated NaCl solution and the mixture was acidified with 1M HCl to pH=1 (43 mL). The water phase was extracted with dichloromethane twice; the combined organic phases were washed with saturated NaHCO₃ solution, saturated NaCl solution and dried (Na₂SO₄). The solvent was evaporated under reduced pressure and the product was recrystallized from methanol to give 4.95 g (19,2 mmol) of the solid brown compound.

η=49%

$T_{tal}$=178-179° C.

| 3-benzyloxycarbonylamino-6-methyl-2-pyridonone | |
| --- | --- |
| ANALYSIS | RESULTS |
| IR (KBr) | ν[cm⁻¹] = 3390, 2798, 1730, 1647, 1522, 1471, 1201, 1042, 753, 698 |
| MS (El) | m/z (%) = 258 (M⁺, 25), 91 (100) |
| NMR CDCl₃, 300 MHz | δ[ppm] = 2.32(s, 3H, CH₃), 5.23(s, 2H, PhCH₂), 6.09(d, 1H, J=7.53Hz, pyridinone H-5), 7.34-7.46(m, 5H, Ph), 7.69(broad s, 1H, NHCOO), 8.07(d, 1H, J=7.16Hz, pyridinone H-4). |

Step 2: Synthesis of tert-butyl 2-[3-{[(benzyloxy)carbonyl]amino}-6-methyl-2-oxo-1(2H)-pyridinyl]acetate

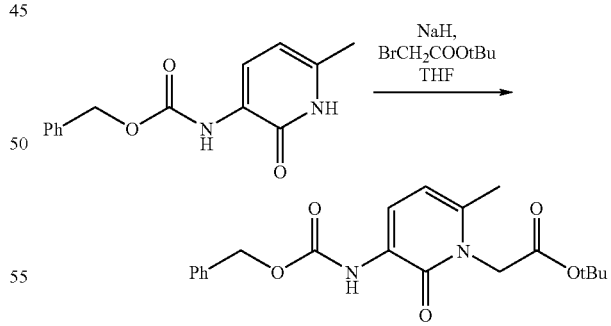

A mixture of 3-benzyloxycarbonylamino-6-methyl-2-pyridinone (4.91 g, 19.0 mmol) in anhydrous THF (50 mL) was cooled to 0° C. and NaH (0.50 g, 20.9 mmol) was added while stirring. To the resulting solution was added t-Bu-bromoacetate (4.3 mL, 25.7 mmol) and after several minutes the precipitate formed. While stirring the reaction mixture was slowly warmed to room temperature. After 3 hours the solvent was evaporated under reduced pressure, 1:1 water/saturated NaCl solution (20 mL) was added to the residue and extracted with 6:1 THF/CH$_2$Cl$_2$ (65 mL). The organic phase was dried (Na$_2$SO$_4$) and the solvent evaporated under reduced pressure. Hexane was added to this solid product and filtered to give 6.19 g (16.6 mmol) of the brown-grey solid compound.

η=87%

T$_{tal}$=127-130° C.

| tert-butyl 2-[3-{[(benzyloxy)carbonyl]amino}-6-methyl-2-oxo-1(2H)-pyridinyl]acetate | |
|---|---|
| ANALYSIS | RESULT |
| IR (KBr) | ν[cm$^{-1}$] = 3234, 2954, 1748, 1718, 1654, 1530, 1366, 1219, 1149, 1058, 974, 778, 567 |
| MS (EI) | m/z (%) = 372 (M$^+$, 33), 91 (100) |
| NMR CDCl$_3$, 300 MHz | δ[ppm] = 1.49(s, 9H, t-Bu), 2.27(s, 3H, CH$_3$), 4.76(s, 2H, PhCH$_2$), 5.21(s, 2H, NCH$_2$), 6.11(d, 1H, J=8.29Hz, pyridinone H-5), 7.32-7.40(m, 5H, Ph), 7.77(broad s, 1H, NHCOO), 7.96(d, 1H, J=7.92Hz, pyridinone H-4). |

Step 3: Synthesis of tert-butyl 2-[3-amino-6-methyl-2-oxo-1(2H)-pyridinyl]acetate

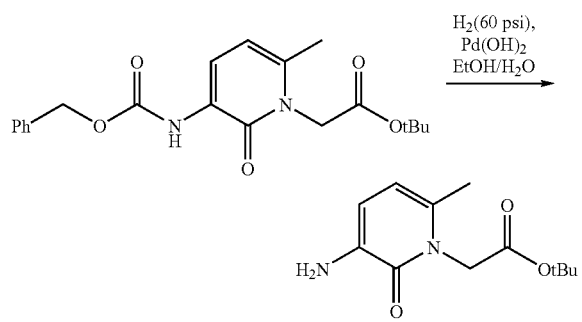

To tert-butyl 2-[3-{[(benzyloxy)carbonyl]amino}-6-methyl-2-oxo-1(2H)-pyridinyl]acetate (6.19 g, 16.6 mmol) in the reactor a mixture of 4:1 ethanol/water (77 mL) was added and degassed with argon for several minutes. During degassing Pd(OH)$_2$ (0.613 g) was added and subjected to catalytic hydrogenation in the reactor containing a hydrogenating agent under the conditions: p(H$_2$)=100 psi, t=2 h. The reaction mixture was filtered through Celite and the solvent evaporated under reduced pressure. To obtain a solid ethanol was added to the resulting material several times and the azeotropic mixture with water was distilled under reduced pressure to give 3.18 g (13.4 mmol) of a grey compound.

η=79%

T$_{tal}$=97-100° C.

| tert-butyl 2-[3-amino-6-methyl-2-oxo-1(2H)-pyridinyl]acetate | |
|---|---|
| ANALYSIS | RESULT |
| IR (KBr) | ν[cm$^{-1}$] = 3434, 3324, 2976, 1746, 1649, 1595, 1357, 1233, 1152, 785 |
| MS (EI) | m/z (%) = 238 (M$^+$, 25), 182 (100) |
| NMR CDCl$_3$, 300 MHz | δ[ppm] = 1.50(s, 9H, t-Bu), 2.21(s, 3H, CH$_3$), 4.06(broad s, 2H, NH$_2$), 4.78(s, 2H, NCH$_2$), 5.93(d, 1H, J=7.16Hz, pyridinone H-5), 6.51(d, 1H, J=7.16Hz, pyridinone H-4). |

Step 4: Synthesis of tert-butyl 2-[3-[(benzylsulfonyl)amino]-6-methyl-2-oxo-1(2H)-pyridinyl]acetate

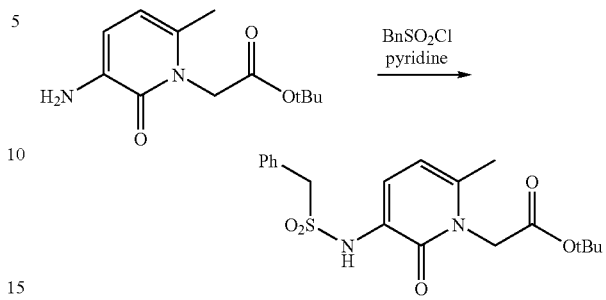

To a solution of tert-butyl 2-[3-amino-6-methyl-2-oxo-1(2H)-pyridinyl]acetate (3.04 g, 12.1 mmol) in pyridine (30 mL) cooled to 0° C. was added benzylsulfonylchloride (2.67 g, 15.1 mmol). While stirring of the reaction mixture the precipitate formed. After one hour the solvent was evaporated under reduced pressure and the product was partitioned between dichloromethane and 10% KHSO$_4$ solution. The aqueous phase was extracted with dichloromethane twice. The combined organic phases were dried over a drying agent and the solvent was evaporated under reduced pressure. A brown-reddish product obtained was suspended in ethyl acetate and heated to reflux, then cooled and filtered to give 2.56 g (6.52 mmol) of a pink product.

η=51%

T$_{tal}$=177-180° C.

| tert-butyl 2-[3-[(benzylsulfonyl)amino]-6-methyl-2-oxo-1(2H)-pyridinyl]acetate | |
|---|---|
| ANALYSIS | RESULTS |
| IR (KBr) | ν[cm$^{-1}$] = 3149, 1740, 1652, 1598, 1454, 1365, 1230, 1137, 887, 771, 540 |
| MS (EI) | m/z (%) = 392 (M$^+$, 35), 181 (100) |
| NMR CDCl$_3$, 300 MHz | δ[ppm] = 1.53(s, 9H, t-Bu), 2.28(s, 3H, CH$_3$), 4.33(s, 2H, PhCH$_2$), 4.77(s, 2H, NCH$_2$), 6.03(d, 1H, J=7.54Hz, pyridinone H-5), 7.22-7.36(m, 7H, Ph, pyridinone H-4, SO$_2$NH). |

Step 5: Synthesis of 2-[3-[(benzylsulfonyl)amino]-6-methyl-2-oxo-1(2H)-pyridinyl]acetic acid

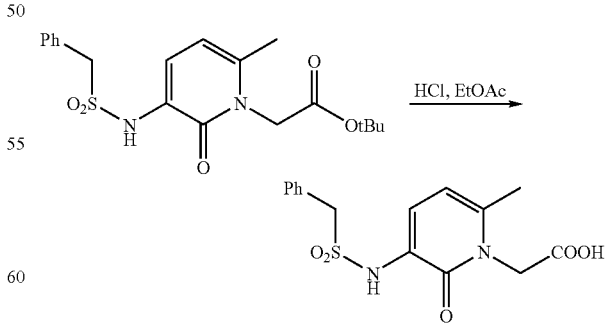

HCl gas was bubbled at 0° C. into a stirred suspension of tert-butyl 2-[3-[(benzylsulfonyl)amino]-6-methyl-2-oxo-1(2H)-pyridinyl]acetate (2.32 g, 5.91 mmol) in ethylacetate until the solution was completed. The HCl-saturated solution was stirred for further one hour at room temperature to form the thick precipitate. The product was collected by filtration to give 1.95 g (5.80 mmol) of a pale pink compound.

η=98%
$T_{tal}$=184-187° C.

| 2-[3-[(benzylsulfonyl)amino]-6-methyl-2-oxo-1(2H)-pyridinyl]acetic acid | |
|---|---|
| ANALYSIS | RESULTS |
| IR (KBr) | ν[cm$^{-1}$] = 3145, 1713, 1654, 1601, 1457, 1368, 1258, 1150, 1030, 877, 698, 540 |
| MS (El) | m/z (%) = 336 (M$^+$, 30), 91 (100) |
| NMR CDCl$_3$, 300 MHz | δ[ppm] = 2.27(s, 3H, CH$_3$), 4.52(s, 2H, PhCH$_2$), 4.78(s, 2H, NCH$_2$), 6.10(d, 1H, J=8.29Hz, pyridinone H-5), 7.13(d, 1H, J=7.54Hz, pyridinone H-4), 7.31-7.37(m, 5H, Ph), 8.63(s, 1H, NHSO$_2$). |

Step 6: Synthesis of (±)-2-[3-[(benzylsulfonyl)amino]-6-methyl-2-oxo-1(2H)pyridinyl]-N-(4,5,6,7-tetrahydro-2H-indazol-5-yl)acetamide To a solution of 2-[3-[(benzylsulfonyl)amino]-6-methyl-2-oxo-1(2H)-pyridinyl]acetic acid (94.1 mg, 0.28 mmol) and 4,5,6,7-tetrahydro-2H-indazol-5-ylamine dihydrochloride (58.8 mg, 0.28 mmol) in 1 mL of DMF was added HOBt (42.8 mg, 0.28 mmol). The pH of the solution was adjusted to 8 with N-methylmorpholine and EDC (53.7 mg, 0.28 mmol) was added. The reaction mixture was stirred at room temperature overnight. The solvent was evaporated, and ethylacetate and saturated NaHCO$_3$ solution were added to the residue. The water phase was extracted with ethyl acetate three times, and the combined organic phases were washed with saturated NaCl solution, dried over MgSO$_4$, filtered and the solvent evaporated under reduced pressure. The product was purified by column chromatography (silicagel, eluant CH$_2$Cl$_2$/MeOH=9/1) to give 48 mg (38%) of a white solid compound.

η=38%
$T_{tal}$=187-190° C.

| (±)-2-[3-[(benzylsulfonyl)amino]-6-methyl-2-oxo-1(2H)pyridinyl]-N-(4,5,6,7-tetrahydro-2H-indazol-5-yl)acetamide | |
|---|---|
| ANALYSIS | RESULTS |
| IR (KBr) | ν[cm$^{-1}$] = 3290, 2936, 1652, 1567, 1445, 1360, 1154, 879, 694, 546 |
| MS (FAB) | m/z (%) = 456 (MH$^+$, 53), 154 (100) |
| NMR, DMSO-d$_6$, 300 MHz | δ[ppm] = 1.71-1.81, 1.87-1.98, 2.34-2.45, 2.57-2.85(4×m, 6H, 4-CH$_2$, 6-CH$_2$, 7-CH$_2$), 2.25(s, 3H, CH$_3$-6'), 3.90-4.04(m, 1H, CH-5), 4.51(s, 2H, PhCH$_2$), 4.72(s, 2H, NCH$_2$), 6.08(d, 1H, J=7.54Hz, CH-5'), 7.12(d, 1H, J=7.53Hz, CH-4'), 7.32-7.37(m, 5H, Ph), 7.96(s, 1H, CH-3), 8.32(d, 1H, J=7.16Hz, CONH), 8.53(broad s, 1H, SO$_2$NH), 12.31(broad s, 1H, NH-2) |

| CHN for C$_{22}$H$_{25}$N$_5$O$_4$S×0.5H$_2$O | Calculated | Found |
|---|---|---|
| % C | 56.88% | 57.07 |
| % H | 5.64% | 5.54 |
| % N | 15.08% | 14.84 |

EXAMPLE 2

Synthesis of (±)-2-[3-[(benzylsulfonyl)amino]-6-metyl-2-oxo-1(2H)pyridinyl]-N-(2-methyl-4,5,6,7-tetrahydro-2H-indazol-5-yl)acetamide The title compound was prepared from 2-[3-[(benzylsulfonyl)amino]-6-methyl-2-oxo-1(2H)-pyridinyl]acetic acid and 2-methyl-4,5,6,7-tetrahydro-2H-indazol-5-ylamine hydrochloride using the procedure of EXAMPLE 1 (STEP 6), and was obtained as a faint yellow solid compound.

η=63%
$T_{tal}$=203-208° C.

| (±)-2-[3-[(benzylsulfonyl)amino]-6-methyl-2-oxo-1(2H)pyridinyl]-N-(2-methyl-4,5,6,7-tetrahydro-2H-indazol-5-yl)acetamide | |
|---|---|
| ANALYSIS | RESULTS |
| IR (KBr) | ν[cm$^{-1}$] = 3311, 3129, 2934, 1657, 1608, 1536, 1455, 1366, 1222, 1140, 1023, 882, 791, 696, 541 |
| MS (FAB) | m/z (%) = 470 (MH$^+$, 100) |
| NMR CDCl$_3$, 300 MHz | δ[ppm] = 1.87-2.05, 2.48-2.56, 2.73-2.80, 2.88-2.95(4×m, 6H, CH$_2$-4, CH$_2$-6, CH$_2$-7), 2.45(s, 3H, CH$_3$-6'), 3.83(s, 3H, CH$_3$-2), 4.15-4.25(m, 1H, CH-5), 4.29(s, 2H, PhCH$_2$), 4.50(s, 2H, NCH$_2$), 6.07(d, 1H, J=7.91Hz, CH-5'), 6.80(d, 1H, J=7.53Hz, CONH), 7.05(s, 1H, CH-3), 7.21-7.37(m, 6H, Ph, SO$_2$NH), 7.37(d, 1H, J=7.91Hz, CH-4'). |

| CHN for C$_{23}$H$_{27}$N$_5$O$_4$S | Calculated | Found |
|---|---|---|
| % C | 58.83% | 58.80% |
| % H | 5.80% | 5.79% |
| % N | 14.91% | 14.58% |

EXAMPLE 3

Synthesis of (±)-2-[3-[(benzylsulfonyl)amino]-6-methyl-2-oxo-1(2H)pyridinyl]-N-(4,5,6,7-tetrahydro-2H-indazol-5-ylmethyl)acetamide

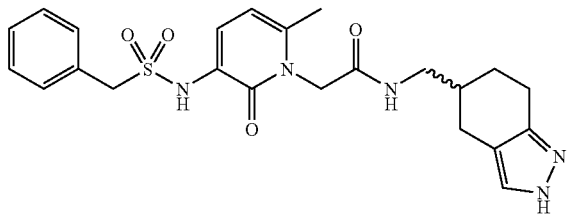

The title compound was prepared from 2-[3-[(benzylsulfonyl)amino]-6-methyl-2-oxo-1(2H)-pyridinyl]acetic acid and 4,5,6,7-tetrahydro-2H-indazol-5-ylmethanamine dihydrochloride using the procedure of EXAMPLE 1 (STEP 6), and was obtained as a white solid compound.

η=62%
$T_{tai}$=105-107° C.

| (±)-2-[3-[(benzylsulfonyl)amino]-6-methyl-2-oxo-1(2H)pyridinyl]-N-(4,5,6,7-tetrahydro-2H-indazol-5-ylmethyl)acetamide | | | |
|---|---|---|---|
| ANALYSIS | RESULTS | | |
| IR (KBr) | ν[cm$^{-1}$] = 3302, 2925, 1649, 1569, 1445, 1361, 1152, 768, 541 | | |
| MS (FAB) | m/z (%) = 470 (MH$^+$, 100) | | |
| NMR CDCl$_3$, 300 MHz | δ[ppm] = 1.42-1.56(m, 1H, CH-5), 1.88-2.01(m, 2H, CH$_2$-6), 2.17-2.26, 2.51-2.61, 2.65-2.78(3×m, 4H, CH$_2$-4, CH$_2$-7), 2.46(s, 3H, CH$_3$-6'), 3.21-3.38(m, 2H, CONHCH$_2$), 4.29(s, 2H, PhCH$_2$), 4.54(s, 2H, NCH$_2$), 6.08(d, 1H, J=7.92Hz, CH-5'), 7.12-7.29(m, 7H, Ph, SO$_2$NH, CONH), 7.39(d, 1H, J=7.54Hz, CH-4'), 8.03(broad s, 1H, CH-3). | | |
| CHN for C$_{23}$H$_{27}$N$_5$O$_4$S×0.5H$_2$O | | Calculated' | Found |
| | % C | 57.72% | 57.64% |
| | % H | 5.90% | 5.93% |
| | % N | 14.63% | 14.23% |

EXAMPLE 4

Synthesis of (±)-2-[3-[(benzylsulfonyl)amino]-6-methyl-2-oxo-1(2H)pyridinyl]-N-[(2-methyl-4,5,6,7-tetrahydro-2H-indazol-5-yl)methyl]acetamide

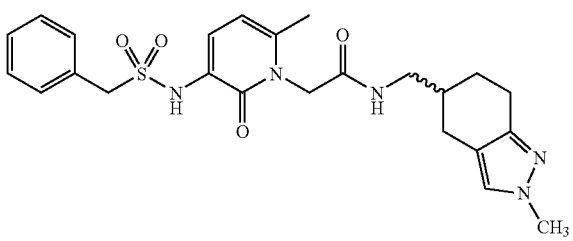

The title compound was prepared from 2-[3-[(benzylsulfonyl)amino]-6-methyl-2-oxo-1(2H)-pyridinyl]acetic acid and 2-methyl-4,5,6,7-tetrahydro-2H-indazol-5-ylmethanamine hydrochloride using the procedure of EXAMPLE 1 (STEP 6), and was obtained as a faint yellow solid compound.

η=64%
$T_{tai}$=105-107° C.

| (±)-2-[3-[(benzylsulfonyl)amino]-6-methyl-2-oxo-1(2H)pyridinyl]-N-[(2-methyl-4,5,6,7-tetrahydro-2H-indazol-5-yl)methyl]acetamide | | | |
|---|---|---|---|
| ANALYSIS | RESULTS | | |
| IR (KBr) | ν[cm$^{-1}$] = 3327, 3118, 2922, 1656, 1611, 1452, 1366, 1145, 870, 775, 547 | | |
| MS (FAB) | m/z (%) = 484 (MH$^+$, 100) | | |
| NMR CDCl$_3$, 300 MHz | δ[ppm] = 1.46-1.54(m, 1H, CH-5), 1.88-2.03(m, 2H, CH$_2$-6), 2.13-2.25, 2.53-2.82(2×m, 4H, CH$_2$-4, CH$_2$-7), 2.46(s, 3H, CH$_3$-6'), 3.22-3.38(m, 2H, CONHCH$_2$), 3.78(s, 3H, CH$_3$-2), 4.29(s, 2H, PhCH$_2$), 4.53(s, 2H, NCH$_2$), 6.07(d, 1H, J=7.54Hz, CH-5'), 6.95(broad d, 1H, CONH), 6.98(s, 1H, CH-3), 7.71-7.30(m, 5H, Ph), 7.38(d, 1H, J=7.54Hz, CH-4'), 8.03(broad s, 1H, SO$_2$NH). | | |
| CHN for C$_{24}$H$_{29}$N$_5$O$_4$S | | Calculated | Found |
| | % C | 59.61 | 59.05 |
| | % H | 6.04 | 6.02 |
| | % N | 14.48 | 13.71 |

EXAMPLE 5

Synthesis of (±)-N-[(2-amino-5,6,7,8-tetrahydro-6-quinazolinyl)methyl]-2-[3-[(benzyl-sulfonyl)amino]-6-methyl-2-oxo-1(2H)-pyridinyl]acetamide

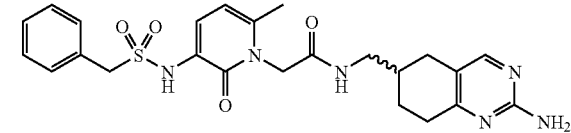

The title compound was prepared from 2-[3-[(benzylsulfonyl)amino]-6-methyl-2-oxo-1(2H)-pyridinyl]acetic acid and 6-(aminomethyl)-5,6,7,8-tetrahydro-2-quinazolinamine using the procedure of EXAMPLE 1 (STEP 6), and was obtained as a white solid compound.

η=44%
$T_{tai}$=210-213° C.

| (±)-N-[(2-amino-5,6,7,8-tetrahydro-6-quinazolinyl)methyl]-2-[3-[(benzyl-sulfonyl)amino]-6-methyl-2-oxo-1(2H)-pyridinyl]acetamide | |
|---|---|
| ANALYSIS | RESULTS |
| IR (KBr) | ν[cm$^{-1}$] = 3363, 1673, 1644, 1587, 1465, 1355, 1151, 782, 544 |
| MS (FAB) | m/z (%) = 497 (MH$^+$, 45), 55 (100) |
| NMR DMSO-d$_6$, 300 MHz | δ[ppm] = 1.34-1.47(m, 1H, CH-6), 1.78-1.94(m, 2H, CH$_2$-7), 2.27(s, 3H, CH$_3$-6'), 2.13-2.26, 2.54-2.67(2×m, 4H, CH$_2$-5, CH$_2$-8), 3.10-3.18(m, 2H, CONHCH$_2$), 4.51(s, 2H, PhCH$_2$), 4.73(s, 2H, NCH$_2$), 6.08(d, 1H J=7.54Hz, CH-5'), 6.20(s, 2H, NH$_2$-2), 7.13(d, 1H J=7.54Hz, CH-4'), 7.20-7.38(m, 5H, Ph), 7.91(s, 1H, CH-4), 8.33(broad t, 1H, CONH), 8.57(s, 1H, SO$_2$NH). |

EXAMPLE 6

Synthesis of (±)-N-(2-amino-4,5,6,7-tetrahydro-1,3-benzothiazol-6-yl)-2-[3-[(benzylsulfonyl)amino]-6-methyl-2-oxo-1(2H)-pyridinyl]acetamide

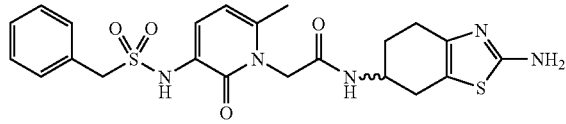

The title compound was prepared from 2-[3-[(benzylsulfonyl)amino]-6-methyl-2-oxo-1(2H)-pyridinyl]acetic acid and 4,5,6,7-tetrahydro-1,3-benzothiazol-2,6-diamine dihydrobromide using the procedure of EXAMPLE 1 (STEP 6), and was obtained as an off-white solid compound.

η=49%

$T_{tal}$=225-229° C.

| (±)-N-(2-amino-4,5,6,7-tetrahydro-1,3-benzothiazol-6-yl)-2-[3-[(benzylsulfonyl)amino]-6-methyl-2-oxo-1(2H)-pyridinyl]acetamide | |
|---|---|
| ANALYSIS | RESULTS |
| IR (KBr) | ν[cm$^{-1}$] = 3429, 3243, 1705, 1648, 1438, 1302, 1158, 781, 696, 565 |
| MS (FAB) | m/z (%) = 488 (MH$^+$, 100) |
| NMR DMSO-d$_6$, 300 MHz | δ[ppm] = 1.69-1.93, 2.42-2.50, 2.52-2.58, 2.72-2.82(4xm, 6H, CH$_2$-4, CH$_2$-5, CH$_2$-7), 2.25(s, 3H, CH$_3$-6'), 4.03-4.07(m, 1H, CH-6), 4.51(s, 2H, PhCH$_2$), 4.71(s, 2H, NCH$_2$), 6.08(d, 1H J=7.53 Hz, CH-5'), 6.66(s, 2H, NH$_2$-2), 7.12(d, 1H, J=7.53 Hz, CH-4'), 7.32-7.37(m, 5H, Ph), 8.38(d, 1H, J=7.54 Hz, CONH), 8.54(s, 1H, SO$_2$NH). |

EXAMPLE 7

Synthesis of (±)-N-[(2-amino-4,5,6,7-tetrahydro-1,3-benzothiazol-6-yl)methyl]-2-[3-[(benzylsulfonyl)amino]-6-methyl-2-oxo-1(2 H)-pyridinyl]acetamide

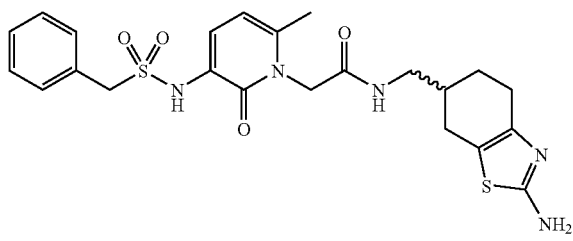

The title compound was prepared from 2-[3-[(benzylsulfonyl)amino]-6-methyl-2-oxo-1(2H)-pyridinyl]acetic acid and 6-(aminomethyl)-4,5,6,7-tetrahydro-1,3-benzothiazol-2-amine dihydrobromide using the procedure of EXAMPLE 1 (STEP 6), and was obtained as a pale solid.

η=41%

| (±)-N-[(2-amino-4,5,6,7-tetrahydro-1,3-benzothiazol-6-yl)methyl]-2-[3-[(benzylsulfonyl)amino]-6-methyl-2-oxo-1(2H)-pyridinyl]acetamide | |
|---|---|
| ANALYSIS | RESULTS |
| IR (KBr) | ν[cm$^{-1}$] = 3433, 1658, 1600, 1444, 1353, 1152, 789 |
| MS (FAB) | m/z (%) = 502 (MH$^+$, 36), 154 (100) |
| NMR CDCl$_3$, 300 MHz | δ[ppm] = 1.25-1.35(m, 1H, CH-6), 1.85-1.93, 2.02-2.13, 2.20-2.30, 2.51-2.77(4xm, 6H, CH$_2$-4, CH$_2$-5, CH$_2$-7), 2.48(s, 3H, CH$_3$-6'), 3.20-3.38(m, 2H, CONHCH$_2$), 4.33(s, 2H, PhCH$_2$), 4.63(s, 2H, NCH$_2$), 6.04(d, 1H, J=7.53 Hz, CH-5'), 7.12(broad s, 1H, NHCO), 7.21-7.33(m, 7H, Ph, CH-4', NHSO$_2$). |

EXAMPLE 8

Synthesis of (±)-2-[3-[(benzylsulfonyl)amino]-6-methyl-2-oxo-1(2H)-pyridinyl]-N-(5,6,7,8-tetrahydro-6-quinazolinylmethyl)acetamide

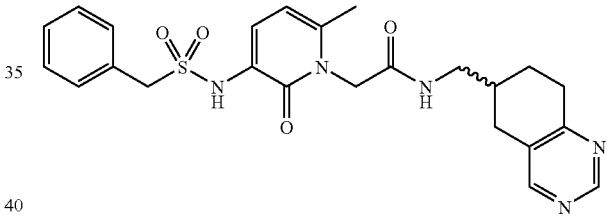

The title compound was prepared from 2-[3-[benzylsulfonyl)amino]-6-methyl-2-oxo-1(2H)-pyridinyl]acetic acid and 6-(aminomethyl)-5,6,7,8-tetrahydroquinazoline using the procedure of EXAMPLE 1 (STEP 6), and was obtained as a white solid.

η=60%

| (±)-2-[3-[(benzylsulfonyl)amino]-6-methyl-2-oxo-1(2H)-pyridinyl]-N-(5,6,7,8-tetrahydro-6-quinazolinylmethyl)acetamide | |
|---|---|
| ANALYSIS | RESULTS |
| IR (KBr) | ν[cm$^{-1}$] = 3374, 1648, 1560, 1457, 1400, 1362, 1152, 894, 778, 698, 544 |
| MS (FAB) | m/z (%) = 482 (MH$^+$, 37), 154 (100) |
| NMR DMSO-d$_6$, 300 MHz | δ[ppm] = 1.53-1.66(m, 1H, CH-6), 1.94-2.13(m, 2H, CH$_2$-7), 2.41-2.13, 2.82-2.98(2xm, 4H, CH$_2$-5, CH$_2$-8), 2.47(s, 3H, CH$_3$-6'), 3.17-3.39(m, 2H, CONHCH$_2$), 4.29(s, 2H, PhCH$_2$), 4.51(s, 2H, NCH$_2$), 6.07(d, 1H, J=7.54Hz, CH-5'), 7.11-7.26(m, 6H, Ph, NHCO), 7.36(d, 1H, J=7.54Hz, CH-4'), 8.30(broad s, 1H, NHSO$_2$), 8.36(s, 1H, CH-4), 8.89(s, 1H, CH-2). |

EXAMPLE 9

Synthesis of (±)-2-[3-{[(2-chloro-4-fluorobenzyl)sulfonyl]amino}-6-methyl-2-oxo-1(2H)-pyridinyl]-N-(4,5,6,7-tetrahydro-2H-indazol-5-ylmethyl)acetamide

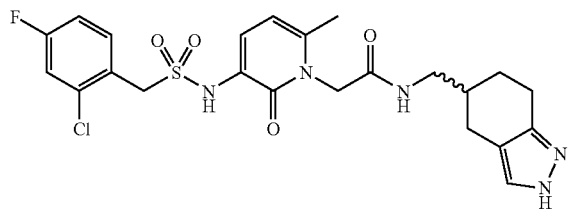

Step 1: Synthesis of (2-chloro-4-fluorophenyl)methanesulfonyl chloride

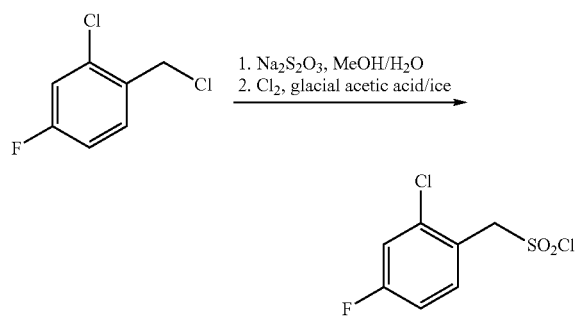

A mixture of 2-chloro-4-fluorobenzyl chloride (7 g, 39.1 mmol) and sodium thiosulfate pentahydrate (9.7 g, 39.1 mmol) in methanol (11 mL) and H$_2$O (11 mL) was heated to reflux for 3 h. The mixture was cooled to 0° C. and glacial acetic acid (11 mL) and ice were added. Chlorine gas was bubbled through the resulting solution for 1 h, periodically adding ice to maintain an ice/liquid mixture. After an additional hour, the reaction was extracted with ether and the ether layer was washed with 5% sodium hydrogen sulphate solution and water, dried (Na$_2$SO$_4$), filtered, and evaporated under reduced pressure to give 9.3 g (37.5 mmol) of the title compound as a colourless solid.

η=98%

| (2-chloro-4-fluorophenyl)methanesulfonyl chloride | |
|---|---|
| ANALYSIS | RESULTS |
| NMR CDCl$_3$, 300 MHz | δ[ppm] = 5.09(s, 2H, CH$_2$SO$_2$), 7.13(ddd, 1H, J=2.63Hz, J=8.11Hz, J=8.10Hz, CH-5), 7.29(dd, 1H, J=2.63Hz, J=8.29Hz, CH-3), 7.62(dd, 1H, J=5.66Hz, J=8.67Hz, CH-6). |

Step 2: Synthesis of tert-butyl 2-[3-{[(2-chloro-4-fluorobenzyl)sulfonyl]amino}-6-methyl-2-oxo-1(2H)-pyridinyl]acetate

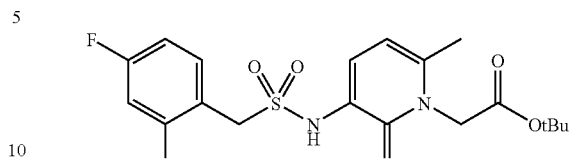

To a solution of tert-butyl 2-[3-amino-6-methyl-2-oxo-1(2H)-pyridinyl]acetate (EXAMPLE 1, STEP 1-3), (1.0 g, 4.2 mmol) in dichloromethane (12 mL) and triethylamine (1 mL) cooled to 0° C. (2-chloro-4-fluorophenyl)methanesulfonyl chloride (1.2 g, 5.0 mmol) was added in portions. After two hours 10% KHSO$_4$ solution (12 mL) was added. The aqueous phase was extracted with dichloromethane twice. The pooled organic phases were dried over a drying agent and the solvent was evaporated under reduced pressure. The product was purified by column chromatography (silicagel, eluant CH$_2$Cl$_2$/MeOH=30/1) to give 0.77 g (1.73 mmol) of a white solid compound.

η=41%

| tert-butyl 2-[3-{[(2-chloro-4-fluorobenzyl)sulfonyl]amino}-6-methyl-2-oxo-1(2H)-pyridinyl]acetate | |
|---|---|
| ANALYSIS | RESULTS |
| IR (KBr) | ν[cm$^{-1}$] = 3128, 2982, 1742, 1652, 1594, 1493, 1447, 1356, 1236, 1157, 918, 856, 771, 596, 493 |
| MS (FAB) | m/z (%) = 445 (MH$^+$, 50), 55 (100) |
| NMR CDCl$_3$, 300 MHz | δ[ppm] = 1.52(s, 9H, t-Bu), 2.30(s, 3H, CH$_3$-6'), 4.53(s, 2H, PhCH$_2$), 4.77(s, 2H, NCH$_2$), 6.06(d, 1H, J=6.79Hz, CH-5'), 6.95-7.03(m, 1H, CH-5), 7.15(dd, 1H, J=2.64Hz, J=8.67Hz, CH-3), 7.32(broad s, 1H, SO$_2$NH), 7.39-7.45(m, 2H, CH-4', CH-6). |

Step 3: Synthesis of 2-[3-{[(2-chloro-4-fluorobenzyl)sulfonyl]amino}-6-methyl-2-oxo-1(2H)-pyridinyl]acetic acid

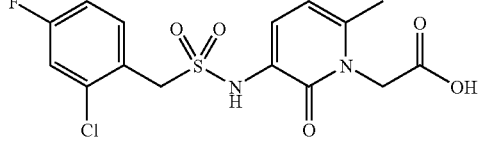

The title compound was prepared from tert-butyl 2-[3-{[(2-chloro-4-fluorobenzyl)sulfonyl]amino}-6-methyl-2-oxo-1(2H)-pyridinyl]acetate using the procedure of EXAMPLE 1 (STEP 5), and was obtained as a white solid compound.

η=95%

| 2-[3-{[(2-chloro-4-fluorobenzyl)sulfonyl]amino}-6-methyl-2-oxo-1(2H)-pyridinyl]acetic acid | |
|---|---|
| ANALYSIS | RESULTS |
| IR (KBr) | ν[cm$^{-1}$] = 3247, 2938, 1716, 1657, 1603, 1493, 1440, 1358, 1232, 1148, 1040, 916, 852, 774, 595 |

-continued

| 2-[3-{[(2-chloro-4-fluorobenzyl)sulfonyl]amino}-6-methyl-2-oxo-1(2H)-pyridinyl]acetic acid | |
|---|---|
| ANALYSIS | RESULTS |
| MS (FAB) | m/z (%) = 388 (MH⁺, 24), 181 (100) |
| NMR<br>DMSO-d₆,<br>300 MHz | δ[ppm] = 2.28(s, 3H, CH₃), 4.65(s, 2H, PhCH₂), 4.80(s, 2H, NCH₂), 6.14(d, 1H, J=7.91Hz, CH-5'), 7.19-7.28(m, 1H, CH-4', CH-5), 7.47(dd, 1H, J=2.63Hz, J=9.04Hz, CH-3), 7.58-7.65(m, 1H, CH-6) 8.99(broad s, 1H, SO₂NH). |

Step 4: Synthesis of (±)-2-[3-{[(2-chloro-4-fluorobenzyl)sulfonyl]amino}-6-methyl-2-oxo-1(2H)-pyridinyl]-N-(4,5,6,7-tetrahydro-2H-indazol-5-ylmethyl)acetamide

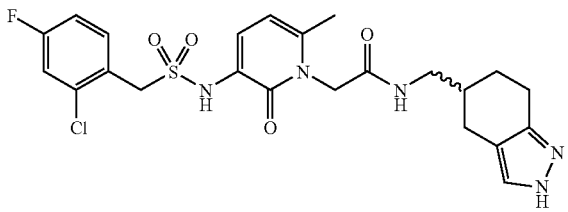

The title compound was prepared from 2-[3-{[(2-chloro-4-fluorobenzyl)sulfonyl]amino}-6-methyl-2-oxo-1(2H)pyridinyl]acetic acid and 4,5,6,7-tetrahydro-2H-indazol-5-ylmethanamine dihydrochloride using the procedure of EXAMPLE 1 (STEP 6), and was obtained as a white solid compound.

η=42%

| (±)-2-[3-{[(2-chloro-4-fluorobenzyl)sulfonyl]amino}-6-methyl-2-oxo-1(2H)-pyridinyl]-N-(4,5,6,7-tetrahydro-2H-indazol-5-ylmethyl)acetamide | |
|---|---|
| ANALYSIS | RESULTS |
| IR (KBr) | ν[cm⁻¹] = 3302, 2924, 1649, 1599, 1571, 1493, 1443, 1364, 1233, 1156, 1041, 915, 797, 594 |
| MS (FAB) | m/z (%) = 522 (MH⁺, 54), 165 (100) |
| NMR<br>CDCl₃,<br>300 MHz | δ[ppm] = 1.42-1.59(m, 1H, CH-5), 1.87-2.01(m, 2H, CH₂-6), 2.17-2.26, 2.55-2.70, 2.71-2.81(3xm, 4H, CH₂-4, CH₂-7), 2.49(s, 3H, CH₃-6'), 3.21-3.40(m, 2H, CONHCH₂), 4.51(s, 2H, PhCH₂), 4.68(s, 2H, NCH₂), 6.11(d, 1H, J=7.91Hz, CH-5'), 6.89-6.97(m, 2H, CH-5", NHCO), 7.08(dd, 1H, J=2.63Hz, J=8.67Hz, CH-3"), 7.27(broad s, 1H, SO₂NH), 7.40-7.47(m, 2H, CH-4', CH-6"). |

EXAMPLE 10

Synthesis of (±)-N-(2-amino-4,5,6,7-tetrahydro-1,3-benzothiazol-6-yl)2-[3-{[(2-chloro-4-fluorobenzyl)sulfonyl]amino}-6-methyl-2-oxo-1(2H)-pyridinyl]acetamide

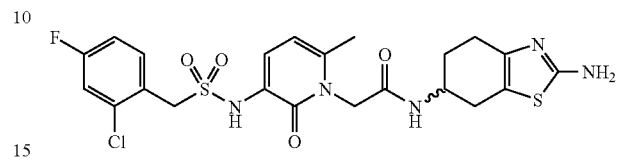

The title compound was prepared from 2-[3-{[(2-chloro-4-fluorobenzyl)sulfonyl]amino}-6-methyl-2-oxo-1(2H)-pyridinyl]acetic acid and 4,5,6,7-tetrahydro-1,3-benzothiazol-2,6-diamine dihydrobromide using the procedure of EXAMPLE 1 (STEP 6), and was obtained as a white solid compound.

η=35%

| (±)-N-(2-amino-4,5,6,7-tetrahydro-1,3-benzothiazol-6-yl)-2-[3-{[(2-chloro-4-fluorobenzyl)sulfonyl]amino}-6-methyl-2-oxo-1(2H)-pyridinyl]acetamide | |
|---|---|
| ANALYSIS | RESULTS |
| IR (KBr) | ν[cm⁻¹] = 3448, 1655, 1606, 1524, 1491, 1442, 1357, 1231, 1147, 1039, 878, 779, 596 |
| MS (FAB) | m/z (%) = (MH⁺,), (100) |
| NMR<br>DMSO-d₆,<br>300 MHz | δ[ppm] = 1.70-1.90, 2.33-2.48, 2.72-2.85(3xm, 6H, CH₂-4, CH₂-5, CH₂-7), 2.26(s, 3H, CH₃-6'), 3.98-4.10(m, 1H, CH-6), 4.65(s, 2H, PhCH₂), 4.73(s, 2H, NCH₂), 6.12(d, 1H J=7.54Hz, CH-5'), 6.65(s, 2H, NH₂-2), 7.20(d, 1H, J=7.54Hz, CH-4'), 7.20-7.27(m, 1H, CH-5"), 7.48(dd, 1H, J=2.64Hz, J=8.67Hz, CH-3"), 7.63(dd, 1H, J=6.41Hz, J=8.67Hz, CH-6"), 8.39(d, 1H, J=7.53Hz, CONH), 8.91(s, 1H, SO₂NH). |

EXAMPLE 11

Synthesis of (±)-2-[6-methyl-2-oxo-3-({[4-(trifluoromethyl)benzyl]sulfonyl}amino)-1(2H)-pyridinyl]-N-(4,5,6,7-tetrahydro-2H-indazol-5-ylmethyl)acetamide

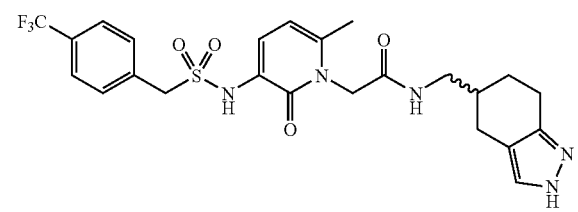

Step 1: Synthesis of [4-(trifluoromethyl)phenyl]methanesulfonyl chloride

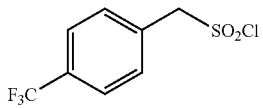

The title compound was prepared from 1-(chloromethyl)-4-(trifluoromethyl)benzene using the procedure of EXAMPLE 9 (STEP 1), and was obtained as a white solid compound.

η=100%

| [4-(trifluoromethyl)phenyl]methanesulfonyl chloride | |
|---|---|
| ANALYSIS | RESULTS |
| IR (KBr) | $\nu[cm^{-1}]$ = 3431, 3004, 1937, 1814, 1619, 1423, 1360, 1325, 1159, 1121, 1069, 1023, 853, 709, 644, 579 |
| NMR CDCl$_3$, 300 MHz | δ[ppm] = 4.92(s, 2H, CH$_2$SO$_2$), 7.65(d, 2H, J=8.28 Hz, CH-2, CH-6), 7.75(d, 2H, J=7.91 Hz, CH-3, CH-5). |

Step 2: Synthesis of tert-butyl 2-[6-methyl-2-oxo-3-({[4-(trifluoromethyl)benzyl]sulfonyl}amino)-1(2H) pyridinyl]acetate

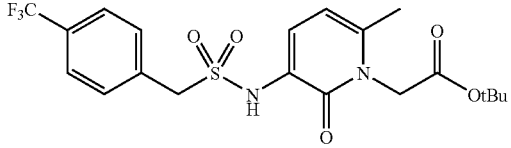

The title compound was prepared from tert-butyl 2-[3-amino-6-methyl-2-oxo-1(2H)-pyridinyl]acetate (EXAMPLE 1, STEP 1-3), and [4-(trifluoromethyl)phenyl]methanesulfonyl chloride using the procedure of EXAMPLE 9 (STEP 2), and was obtained as a white solid compound.

η=32%

| tert-butyl 2-[6-methyl-2-oxo-3-({[4-(trifluoromethyl)benzyl]sulfonyl}amino)-1(2H)-pyridinyl]acetate | |
|---|---|
| ANALYSIS | RESULTS |
| IR (KBr) | $\nu[cm^{-1}]$ = 3232, 2955, 1748, 1718, 1654, 1598, 1530, 1366, 1219, 1149, 1959, 1003, 851, 778, 699 |
| MS (FAB) | m/z (%) = 461 (MH$^+$, 17), 91 (100) |
| NMR CDCl$_3$, 300 MHz | δ[ppm] = 1.49(s, 9H, t-Bu), 2.27(s, 3H, CH$_3$-6'), 4.76(s, 2H, PhCH$_2$), 5.21(s, 2H, NCH$_2$), 6.11(d, 1H, J=7.53Hz, CH-5'), 7.33-7.42(m, 4H, CH—Ph), 7.77(broad s, 1H, SO$_2$NH), 7.96(d, 1H, J=6.78Hz, CH-4'). |

Step 3: Synthesis of 2-[6-methyl-2-oxo-3-({[4-(trifluoromethyl)benzyl]sulfonyl}amino)-1(2H)-pyridinyl]acetic acid

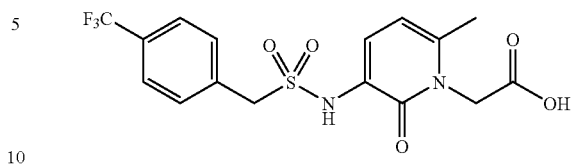

The title compound was prepared from tert-butyl 2-[6-methyl-2-oxo-3-({[4-(trifluoromethyl)benzyl]sulfonyl}amino)-1(2H)-pyridinyl]acetate using the procedure of EXAMPLE 1 (STEP 5), and was obtained as a pail solid compound.

η=90%

| 2-[6-methyl-2-oxo-3-({[4-(trifluoromethyl)benzyl]sulfonyl}amino)-1(2H)-pyridinyl]acetic acid | |
|---|---|
| ANALYSIS | RESULTS |
| IR (KBr) | $\nu[cm^{-1}]$ = 3395, 2960, 1737, 1650, 1557, 1512, 1409, 1182, 1060, 970, 866, 767, 699, 585 |
| MS (FAB) | m/z (%) = 405 (MH$^+$, 58), 55 (100) |
| NMR CDCl$_3$, 300 MHz | δ[ppm] = 2.35(s, 3H, CH$_3$-6'), 4.88(s, 2H, CH$_2$Ph), 5.22(s, 2H, CH$_2$N), 6.21(d, 1H, J=7.16Hz, CH-5'), 7.35-7.42(m, 4H, CH—Ph), 7.73(broad s, 1H, NHSO$_2$), 8.03(d, 1H, J=7.53Hz, CH-4'). |

Step 4: Synthesis of (±)-2-[6-methyl-2-oxo-3-({[4-(trifluoromethyl)benzyl]sulfonyl}amino)-1(2H)pyridinyl]-N-(4,5,6,7-tetrahydro-2H-indazol-5-ylmethyl)acetamide

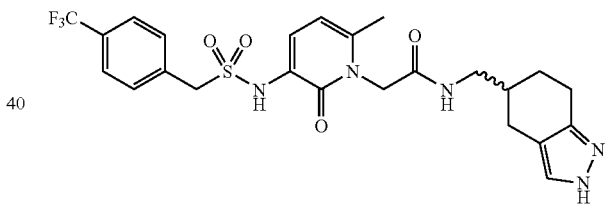

The title compound was prepared from 2-[6-methyl-2-oxo-3-({[4 (trifluoromethyl)benzyl]sulfonyl}amino)-1(2H)-pyridinyl]acetic acid and 4,5,6,7-tetrahydro-2H-indazol-5-ylmethanamine dihydrochloride using the procedure of EXAMPLE 1 (STEP 6), and was obtained as a white solid compound.

η=60%

| (±)-2-[6-methyl-2-oxo-3-({[4-(trifluoromethyl)benzyl]sulfonyl}amino)-1(2H)-pyridinyl]-N-(4,5,6,7-tetrahydro-2H-indazol-5-ylmethyl)acetamide | |
|---|---|
| ANALYSIS | RESULTS |
| IR (KBr) | $\nu[cm^{-1}]$ = 3253, 2923, 1713, 1651, 1606, 1536, 1361, 1221, 1092, 717 |
| NMR CDCl$_3$, 300 MHz | δ[ppm] = 1.39-1.52(m, 1H, CH-5), 1.86-1.97(m, 2H, CH$_2$-6), 2.13-2.22, 2.60-2.69, 2.73-2.82(3×m, 4H, CH$_2$-4, CH$_2$-7), 2.27(s, 3H, CH$_3$-6'), 3.18-3.36(m, 2H, CONHCH$_2$), 4.76(s, 2H, PhCH$_2$), 5.23(s, 2H, NCH$_2$), 6.19(d, 1H, J=8.28Hz, CH-5'), 6.95(broad t, 1H, NHCO), 7.27(s, 1H, CH-3), 7.34-7.45(m, 4H, CH—Ph), 7.74(broad s, 1H, SO$_2$NH), 8.01(d, 1H, J=7.91Hz, CH-4'). |

EXAMPLE 12

Synthesis of (±)-N-(2-amino-4,5,6,7-tetrahydro-1,3-benzothiazol-6 -yl)-2-[6-methyl-2-oxo-3-({[4-trifluoromethyl)benzyl]sulfonyl}amino)-1(2H)-pyridinyl]acetamide

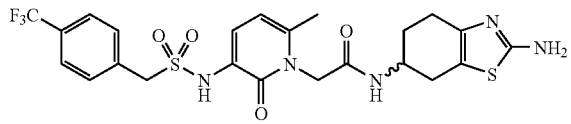

The title compound was prepared from 2-[6-methyl-2-oxo-3-({[4-(trifluoromethyl)benzyl]sulfonyl }amino)-1(2H)-pyridinyl]acetic acid and 4,5,6,7-tetrahydro-1,3 -benzothiazol-2,6-diamine dihydrobromide using the procedure of EXAMPLE 1 (STEP 6), and was obtained as a white solid compound.

η=37%

| (±)-N-(2-amino-4,5,6,7-tetrahydro-1,3-benzothiazol-6-yl)-2-[6-methyl-2-oxo-3-({[4-(trifluoromethyl)benzyl]sulfonyl}amino)-1(2H)-pyridinyl]acetamide | |
|---|---|
| ANALYSIS | RESULTS |
| IR (KBr) | ν[cm$^{-1}$] = 3452, 3386, 3284, 3083, 1732, 1649, 1524, 1416, 1364, 1211, 1090, 849, 697, 618 |
| MS (FAB) | m/z (%) = (MH$^+$,), (100) |
| NMR DMSO-d$_6$, 300 MHz | δ[ppm] = 1.70-1.90, 2.35-2.44, 2.54-2.59, 2.75-2.83(4xm, 6H, CH$_2$-4, CH$_2$-5, CH$_2$-7), 2.24(s, 3H, CH$_3$-6'), 3.96-4.06(m, 1H, CH-6), 4.71(s, 2H, PhCH$_2$), 5.16(s, 2H, NCH$_2$), 6.16(d, 1H J=8.29Hz, CH-5'), 6.64(s, 2H, NH$_2$-2), 7.31-7.45(m, 4H, CH—Ph), 7.72(d, 1H, J=7.92Hz, CH-4'), 8.26(s, 1H, SO$_2$NH), 8.36(d, 1H, J=7.16Hz, CONH). |

EXAMPLE 13

Synthesis of N-(2-amino-4,5,6,7-tetrahydro-1,3-benzothiazol-6-yl)-2-[6-methyl -2-oxo-3-({[3-(trifluoromethyl)benzyl]sulfonyl}amino)-1(2-pyridinyl]acetamide

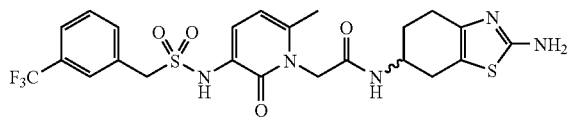

Step 1: Synthesis of [3-(trifluoromethyl)phenyl]methanesulfonyl chloride

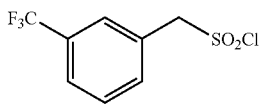

The title compound was prepared from 1-(chloromethyl)-3-(trifluoromethyl)benzene using the procedure of EXAMPLE 9 (STEP 1), and was obtained as a white solid compound.

η=100%

| [3-(trifluoromethyl)phenyl]methanesulfonyl chloride | |
|---|---|
| ANALYSIS | RESULTS |
| NMR CDCl$_3$, 300 MHz | δ[ppm] = 4.94(s, 2H, CH$_2$SO$_2$), 7.60-7.72(m, 4H, CH-Ph). |

Step 2: Synthesis of tert-butyl 2-[6-methyl-2-oxo-3-({[3-(trifluoromethyl)benzyl]sulfonyl}amino)-1(2H)-pyridinyl]acetate

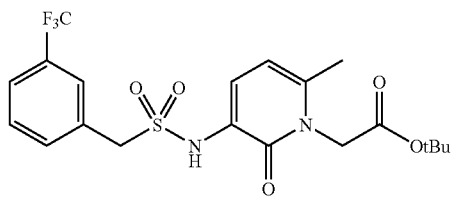

The title compound was prepared from tert-butyl 2-[3-amino-6-methyl-2-oxo-1(2H)-pyridinyl]acetate (EXAMPLE 1, STEP 1-3), and [3-trifluoromethyl)phenyl]methanesulfonyl chloride using the procedure of EXAMPLE 9 (STEP 2), and was obtained as a white solid compound.

η=33%

| tert-butyl 2-[6-methyl-2-oxo-3-({[3-(trifluoromethyl)benzyl]sulfonyl}amino)-1(2H)-pyridinyl]acetate | |
|---|---|
| ANALYSIS | RESULTS |
| IR (KBr) | ν[cm$^{-1}$] = 3152, 2996, 1742, 1651, 1595, 1454, 1334, 1234, 1122, 1073, 1003, 920, 824, 699, 648, 541 |
| MS (FAB) | m/z (%) = 460 (MH$^+$, 90), 182 (100) |
| NMR CDCl$_3$, 300 MHz | δ[ppm] = 1.52(s, 9H, t-Bu), 2.27(s, 3H, CH$_3$-6'), 4.40(s, 2H, PhCH$_2$), 4.76(s, 2H, NCH$_2$), 6.02(d, 1H, J=7.54Hz, CH-5'), 7.38(d, 1H, J=7.53Hz, CH-4'), 7.50-7.70(m, 5H, CH—Ph, NHSO$_2$). |

Step 3: Synthesis of 2-[6-methyl-2-oxo-3-({[3 -(trifluoromethyl)benzyl]sulfonyl}amino)-1(2H)-pyridinyl]acetic acid

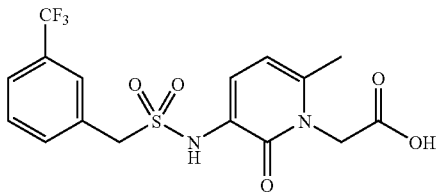

The title compound was prepared from tert-butyl 2-[6-methyl-2-oxo-3 -({[3-(trifluoromethyl) benzyl] sulfonyl}amino)-1(2H)-pyridinyl]acetate using the procedure of EXAMPLE 1 (STEP 5), and was obtained as pail yellow solid compound.

η=93%

| 2-[6-methyl-2-oxo-3-({[3-(trifluoromethyl)benzyl]sulfonyl}amino)-1(2H)-pyridinyl]acetic acid | |
|---|---|
| ANALYSIS | RESULTS |
| IR (KBr) | ν[cm⁻¹] = 3232, 1722, 1657, 1606, 1452, 1333, 1120, 1074, 1003, 920, 810, 701, 544 |
| MS (FAB) | m/z (%) = 404 (MH⁺, 39), 159 (100) |
| NMR CDCl₃, 300 MHz | δ[ppm] = 2.32(s, 3H, CH₃-6'), 4.41(s, 2H, CH₂Ph), 4.86(s, 2H, CH₂N), 6.07(d, 1H, J=8.22Hz, CH-5'), 7.40(d, 1H, J=7.91Hz, CH-4'), 7.52-7.71(m, 5H, CH—Ph, NHSO₂). |

Step 4: Synthesis of (±)-N-(2-amino-4,5,6,7-tetrahydro-1,3-benzothiazol-6-yl)-2-[6-methyl-2-oxo-3-({[3-(trifluoromethyl)benzyl]sulfonyl}amino)-1(2 H)-pyridinyl]acetamide

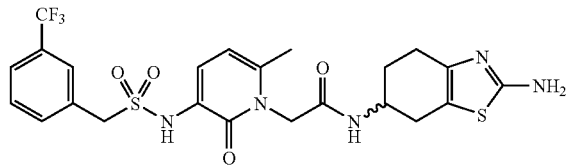

The title compound was prepared from 2-[6-methyl-2-oxo-3-({[3-(trifluoromethyl)benzyl]sulfonyl}amino)-1(2H)-pyridinyl]acetic acid and 4,5,6,7-tetrahydro-1,3-benzothiazol-2,6-diamine dihydrobromide using the procedure of EXAMPLE 1 (STEP 6), and was obtained as a white solid compound.

η=42%

| (±)-N-(2-amino-4,5,6,7-tetrahydro-1,3-benzothiazol-6-yl)-2-[6-methyl-2-oxo-3-({[3-(trifluoromethyl)benzyl]sulfonyl}amino)-1(2H)-pyridinyl]acetamide | |
|---|---|
| ANALYSIS | RESULTS |
| IR (KBr) | ν[cm⁻¹] = 3290, 2934, 1645, 1607, 1531, 1443, 1332, 1148, 1073, 886, 814, 700 |
| MS (FAB) | m/z (%) = (MH⁺,), (100) |
| NMR DMSO-d₆, 300 MHz | δ[ppm] = 1.70-1.90, 2.36-2.43, 2.55-2.59, 2.74-2.84(4×m, 6H, CH₂-4, CH₂-5, CH₂-7), 2.25(s, 3H, CH₃-6'), 3.98-4.09(m, 1H, CH-6), 4.68(s, 2H, PhCH₂), 4.72(s, 2H, NCH₂), 6.08(d, 1H J=7.54Hz, CH-5'), 6.67(s, 2H, NH₂-2), 7.16(d, 1H, J=7.16Hz, CH-4'), 7.58-7.77(m, 4H, CH—Ph), 8.38(d, 1H, J=7.91Hz, CONH), 8.76(s, 1H, SO₂NH). |

EXAMPLE 14

Synthesis of (±)-N-(2-amino-4,5,6,7-tetrahydro-1,3-benzothiazol-6-yl)-2-[3-[(butylsulfonyl)amino]-6-methyl-2-oxo-1(2H)-pyridinyl]acetamide

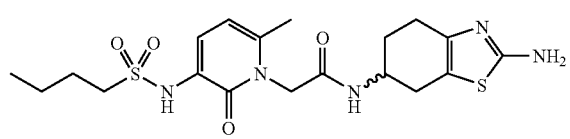

Step 1: Synthesis of tert-butyl 2-[3-[(butylsulfonyl)amino]-6-methyl-2-oxo-1(2H)-pyridinyl]acetate

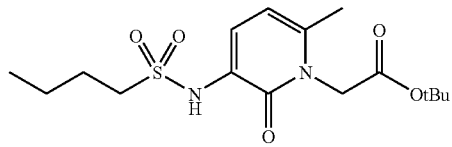

The title compound was prepared from tert-butyl 2-[3-amino-6-methyl-2-oxo-1(2H)-pyridinyl]acetate (EXAMPLE 1, STEP 1-3), and 1-butanesulfonyl chloride using the procedure of EXAMPLE 9 (STEP 2). The product was recrystallized from ethylacetate to give a white crystalline solid compound.

η=49%

| tert-butyl 2-[3-[(butylsulfonyl)amino]-6-methyl-2-oxo-1(2H)-pyridinyl]acetate | |
|---|---|
| ANALYSIS | RESULTS |
| IR (KBr) | ν[cm⁻¹] = 3174, 2973, 1737, 1653, 1600, 1575, 1453, 1357, 1236, 1145, 805, 503 |
| MS (FAB) | m/z (%) = 358 (MH⁺, 100) |
| NMR CDCl₃, 300 MHz | δ[ppm] = 0.91(t, 3H, J=7.16Hz, CH₃), 1.35-1.46(m, 2H, CH₂), 1.50(s, 9H, t-Bu), 1.74-1.85(m, 2H, CH₂), 2.29(s, 3H, CH₃-6'), 3.02-3.08(m, 2H, CH₂), 4.77(s, 2H, NCH₂), 6.10(d, 1H, J=7.54Hz, CH-5'), 7.20(s, 1H, NHSO₂), 7.47(d, 1H, J=7.53Hz, CH-4'). |

Step 2: Synthesis of 2-[3-[(butylsulfonyl)amino]-6-methyl-2-oxo-1(2H)-pyridinyl]acetic acid

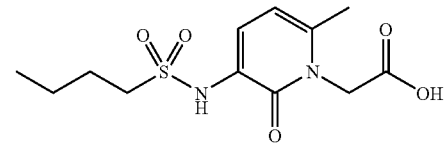

The title compound was prepared from of tert-butyl 2-[3-[(butylsulfonyl)amino]-6-methyl-2-oxo-1(2H)-pyridinyl]acetate using the procedure of EXAMPLE 1 (STEP 5), and was obtained as a white crystalline solid compound.

η=95%

| 2-[3-[(butylsulfonyl)amino]-6-methyl-2-oxo-1(2H)-pyridinyl]acetic acid | |
|---|---|
| ANALYSIS | RESULTS |
| IR (KBr) | ν[cm⁻¹] = 3158, 2938, 1725, 1651, 1604, 1453, 1361, 1248, 1143, 1031, 918, 558 |
| MS (FAB) | m/z (%) = 303 (MH⁺, 100) |
| NMR DMSO-d₆, 300 MHz | δ[ppm] = 0.85(t, 3H, J=7.16Hz, CH₃), 1.26-1.43(m, 2H, CH₂), 1.61-1.72(m, 2H, CH₂), 2.27(s, 3H, CH₃-6'), 3.03-3.11(m, 2H, CH₂), 4.77(s, 2H, NCH₂), 6.17(d, 1H, J=7.54Hz, CH-5'), 7.29(d, 1H, J=7.53Hz, CH-4') 8.68(s, 1H, NHSO₂). |

Step 3: Synthesis of (±)-N-(2-amino-4,5,6,7-tetrahydro-1,3-benzothiazol-6-yl)-2-[3-[(butylsulfonyl)amino]-6-methyl-2-oxo-1(2H)-pyridinyl]acetamide

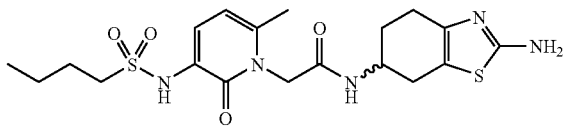

The title compound was prepared from 2-[3-[(butylsulfonyl)amino]-6-methyl-2-oxo-1(2H)-pyridinyl]acetic acid and 4,5,6,7-tetrahydro-1,3-benzothiazol-2,6-diamine dihydrobromide using the procedure of EXAMPLE 1 (STEP 6). The product was recrystallized from methanol to give a pale brown solid compound.

η=40%

| (±)-N-(2-amino-4,5,6,7-tetrahydro-1,3-benzothiazol-6-yl)-2-[3-[(butylsulfonyl)amino]-6-methyl-2-oxo-1(2H)-pyridinyl]acetamide | |
|---|---|
| ANALYSIS | RESULTS |
| IR (KBr) | $\nu[cm^{-1}]$ = 3464, 3324, 3136, 2953, 1649, 1594, 1449, 1354, 1143, 775, 559 |
| MS (FAB) | m/z (%) = 454 (MH$^+$, 49), 154 (100) |
| NMR DMSO-d$_6$, 300 MHz | δ[ppm] = 0.85(t, 3H, J=7.53Hz, CH$_3$), 1.28-1.40(m, 2H, CH$_2$), 1.61-1.72(m, 2H, CH$_2$), 1.73-1.90, 2.33-2.44, 2.53-2.59, 2.72-2.82(4×m, 6H, CH$_2$-4, CH$_2$-5, CH$_2$-7), 2.26(s, 3H, CH$_3$-6'), 3.03-3.10(m, 2H, CH$_2$), 3.95-4.05(m, 1H, CH-6), 4.70(s, 2H, NCH$_2$), 6.13(d, 1H J=7.53Hz, CH-5'), 6.65(s, 2H, NH$_2$-2), 7.27(d, 1H, J=7.54Hz, CH-4'), 8.36(d, 1H, J=7.92Hz, CONH), 8.59(s, 1H, SO$_2$NH). |

EXAMPLE 15

Synthesis of (±)-N-(2-amino-4,5,6,7-tetrahydro-1,3-benzothiazol-6-yl)-2-[6-methyl-2-oxo-3-(phenethylamino)-1(2H)-pyridinyl]acetamide

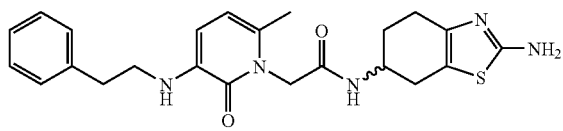

Step 1: Synthesis of tert-butyl 2-[6-methyl-2-oxo-3-(phenethylamino)-1(2H)-pyridinyl]acetate

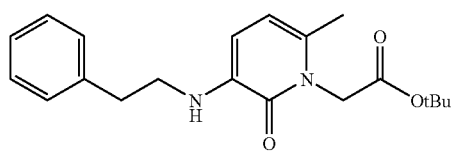

Sodium triacetoxyborohydride (0.67 g, 3.15 mmol) was added to a stirred solution of tert-butyl 2-[3-amino-6-methyl-2-oxo-1(2H)-pyridinyl]acetate (EXAMPLE 1, STEP 1-3), (0.5 g, 2.10 mmol) and phenyl acetaldehyde (0.18 mL, 2.33 mmol) in 0.24 M acetic acid (0.14 mL) in 1,2-dichloroethane (11 mL). After 16 h the mixture was quenched with water and extracted into ethylacetate. The ethyl acetate layer was washed with sodium carbonate solution and brine, dried (Na$_2$SO$_4$) and evaporated under reduced pressure to a glass. The crude product was purified by flash column chromatography (silicagel, eluant CH$_2$Cl$_2$/MeOH=40/1) to give 0.34 g (1.00 mmol) of a light blue solid compound.

η=47%

| tert-butyl 2-[6-methyl-2-oxo-3-(phenethylamino)-1(2H)-pyridinyl]acetate | |
|---|---|
| ANALYSIS | RESULTS |
| IR (KBr) | $\nu[cm^{-1}]$ = 3337, 2976, 1748, 1649, 1596, 1493, 1364, 1156, 943, 700 |
| MS (FAB) | m/z (%) = 343 (MH$^+$, 65), 93 (100) |
| NMR CDCl$_3$, 300 MHz | δ[ppm] = 1.50(s, 9H, t-Bu), 2.21(s, 3H, CH$_3$-6'), 2.88-2.97(m, 2H, CH$_2$), 3.33(t, 2H, J=7.35Hz, CH$_2$), 4.77(s, 2H, NCH$_2$), 4.87(broad s, 1H, NH), 6.00(d, 1H, J=7.16Hz, CH-5'), 6.18(d, 1H, J=7.16Hz, CH-4'), 7.23-7.37(m, 5H, Ph). |

Step 2: Synthesis of 2-[6-methyl-2-oxo-3-(phenethylamino)-1(2H)-pyridinyl]acetic acid

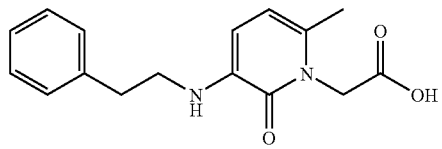

The title compound was prepared from of tert-butyl 2-[6-methyl-2-oxo-3-(phenethylamino)-1(2H)-pyridinyl]acetate using the procedure of EXAMPLE 1 (STEP 5), and was obtained as a yellow solid compound.

η=96%

| 2-[6-methyl-2-oxo-3-(phenethylamino)-1(2H)-pyridinyl]acetic acid | |
|---|---|
| ANALYSIS | RESULTS |
| MS (FAB) | m/z (%) = 287 (MH$^+$, 100) |
| NMR DMSO-d$_6$, 300 MHz | δ[ppm] = 2.17(s, 3H, CH-6'), 2.86(t, 2H, J=7.35Hz, CH$_2$) 3.25(t, 2H, J=7.35Hz, CH$_2$), 4.72(s, 2H, NCH$_2$), 6.02(d, 1H, J=8.29Hz, CH-5'), 6.29(d, 1H, J=7.53Hz, CH-4'), 7.19-7.33(m, 5H, Ph). |

Step 3: Synthesis of (±)-N-(2-amino-4,5,6,7-tetrahydro-1,3-benzothiazol-6-yl)-2-[6-methyl-2-oxo-3-(phenethylamino)-1(2H) pyridinyl]acetamide

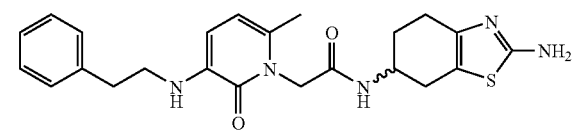

The title compound was prepared from 2-[6-methyl-2-oxo-3-(phenethylamino)-1(2H)-pyridinyl]acetic acid and 4,5,6,7-tetrahydro-1,3-benzothiazol-2,6-diamine dihydrobromide using the procedure of EXAMPLE 1 (STEP 6), and was obtained as a yellow crystalline solid compound.

η=40%

| (±)-N-(2-amino-4,5,6,7-tetrahydro-1,3-benzothiazol-6-yl)-2-[6-methyl-2-oxo-3-(phenethylamino)-1(2H)-pyridinyl]acetamide | |
|---|---|
| ANALYSIS | RESULTS |
| IR (KBr) | ν[cm$^{-1}$] = 3418, 1644, 1593, 1524, 1369, 1333, 1232, 779, 700 |
| MS (FAB) | m/z (%) = 437 (MH$^+$, 65), 269 (100) |
| NMR DMSO-d$_6$, 300 MHz | δ[ppm] = 1.67-1.90, 2.33-2.45, 2.51-2.82(3×m, 6H, CH$_2$-4, CH$_2$-5, CH$_2$-7), 2.15(s, 3H, CH$_3$-6'), 3.94-4.08(m, 1H, CH-6), 4.65(s, 2H, NCH$_2$), 5.02(broad t, 1H, NH), 5.98(d, 1H, J=7.53Hz, CH-5'), 6.22(d, 1H, J=7.53Hz, CH-4'), 6.65(s, 2H, NH$_2$-2), 7.18-7.34(m, 5H, Ph), 8.27(d, 1H, J=7.54Hz, CONH). |

EXAMPLE 16

Synthesis of (±)-2-[6-methyl-2-oxo-3-(phenethylamino)-1(2H)-pyridinyl]-N-(4,5,6,7-tetrahydro-2H-indazol-5-ylmethyl)acetamide

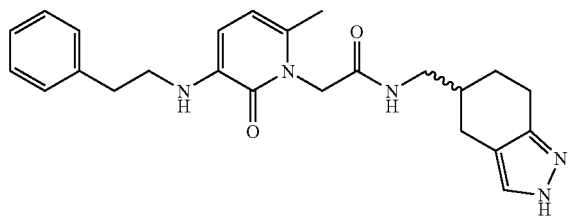

The title compound was prepared from 2-[6-methyl-2-oxo-3-(phenethylamino)-1(2H)-pyridinyl]acetic acid and 4,5,6,7-tetrahydro-2H-indazol-5-ylamine dihydrochloride using the procedure of EXAMPLE 1 (STEP 6), and was obtained as a yellow solid compound.

η=45%

| (±)-2-[6-methyl-2-oxo-3-(phenethylamino)-1(2H)-pyridinyl]-N-(4,5,6,7-tetrahydro-2H-indazol-5-ylmethyl)acetamide | |
|---|---|
| ANALYSIS | RESULTS |
| IR (KBr) | ν[cm$^{-1}$] = 3291, 2924, 1645, 1593, 1492, 1361, 1236, 1112, 960, 752, 701 |
| MS (FAB) | m/z (%) = (MH$^+$,), (100) |
| NMR CDCl$_3$, 300 MHz | δ[ppm] = 1.38-153(m, 1H, CH-5), 1.81-1.97(m, 2H, CH$_2$-6), 2.07-2.20, 2.51-2.81(2×m, 4H, CH$_2$-4, CH$_2$-7), 2.39(s, 3H, CH$_3$-6'), 2.95(t, 2H, J=7.35Hz, CH$_2$), 3.19-3.29(m, 2H, NHCOCH$_2$) 3.34(t, 2H, J=7.16Hz, CH$_2$), 4.75(s, 2H, NCH$_2$), 6.07(d, 1H, J=7.54Hz, CH-5'), 6.23(d, 1H, J=7.53Hz, CH-4'), 7.14(broad t, 1H, NHCO), 7.20-7.35(m, 6H, Ph, CH-3). |

EXAMPLE 17

Results of Tested Compounds Regarding the Inhibiton of Thrombin and Trypsin

| Compound structure | Ki thrombin (μM) | Ki trypsin (μM) | Ki trypsin/ Ki thrombin |
|---|---|---|---|
| 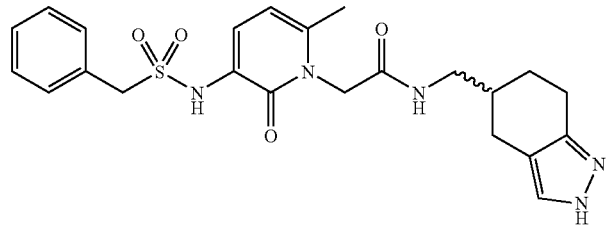 | 0.21 | 376 | 1790 |
| 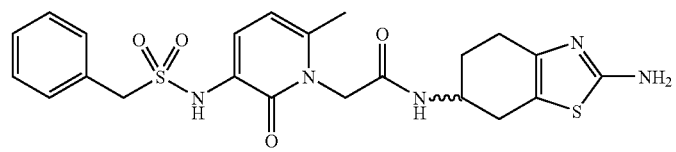 | 0.16 | 260 | 1625 |
| 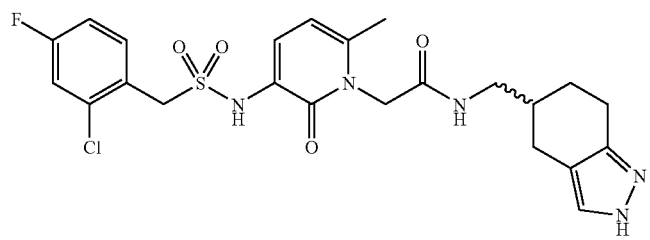 | 0.16 | >300 | >1875 |

| Compound structure | Ki thrombin (μM) | Ki trypsin (μM) | Ki trypsin/ Ki thrombin |
|---|---|---|---|
| 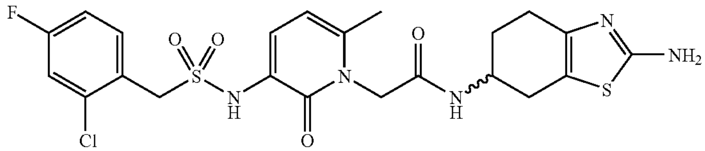 | 0.16 | 193 | 1097 |
| 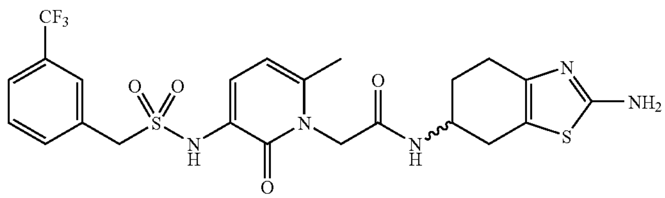 | 0.65 | >200 | >300 |
| 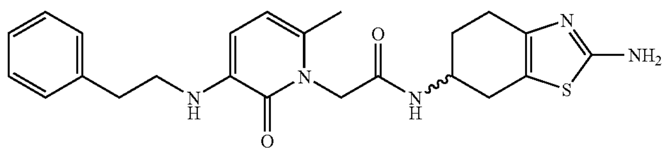 | 0.69 | 147 | 213 |
| 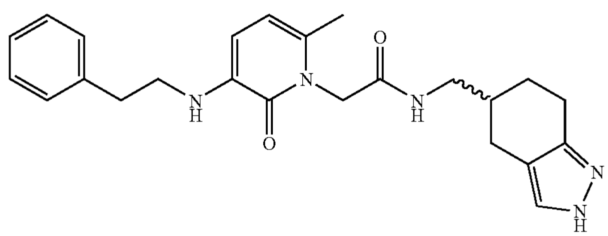 | 0.82 | 421 | 526 |
| 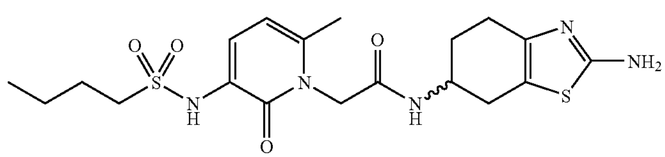 | 1.3 | 50 | 37 |
| 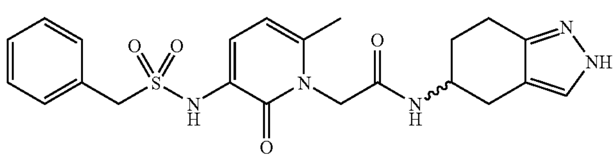 | 4.7 | 438 | 93 |

The invention claimed is:

1. A compound of the formula (I)

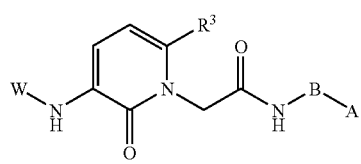

wherein:
W is
R$^1$,
R$^1$OCO,
R$^1$CO,
R$^1$SO$_2$, or
(R$^1$(CH$_2$)$_n$)$_m$NH$_q$CO, where n is 0, 1, 2, 3 or 4,
where m is 1 or 2 and
where q is 0 or 1, with the proviso
that where n is 1, 2, 3 or 4, q is 1 and m is 1, and
where n is 0, m is 1 or 2 and q is 0 or 1,
and wherein R$^1$ can be the same or different;
R$^1$ is
R$^2$(CH$_2$)$_n$, where n is 0, 1, 2, 3 or 4,
(R$^2$)(OR$^2$)CH(CH$_2$)$_p$, where p is 1, 2, 3 or 4,
(R$^2$)$_2$CH(CH$_2$)$_n$, where n is 0, 1, 2, 3 or 4, and R$^2$ can be the same or different, and
R$^2$O(CH$_2$)$_p$, where p is 1, 2, 3 or 4;
R$^2$ is
hydrogen,
phenyl, unsubstituted or substituted with one or more C$_{1-4}$ linear or branched alkyl, C$_{1-4}$ linear or branched alkoxy, halogen, trifluoromethyl, hydroxy, $COOR^4$, $CONHR^4$, nitro, $NHR^4$ or $NR^4R^4$ group(s),
naphthyl,
biphenyl,
$COOR^4$,
$C_{1-4}$ linear or branched alkyl,
$C_{3-7}$ cycloalkyl, or
$C_{7-12}$ bicycloalkyl;
$R^4$ is
hydrogen, or
$C_{1-4}$ linear or branched alkyl;
$R^3$ is
hydrogen,
$C_{1-4}$ linear or branched alkyl,
$C_{3-7}$ cycloalkyl, or
trifluoromethyl group;
B is
$(CH_2)_k$, where k is 0 or 1;
A is

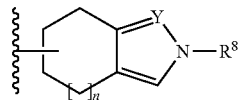

wherein Y is N, n=1, and $R^8$ is hydrogen.

2. A pharmaceutically acceptable salt of a compound of claim 1.

3. A pharmaceutical composition comprising a therapeutically effective amount of a compound of formula (I) according to claim 1 and pharmaceutically acceptable auxiliary substances.

4. A method for inhibiting thrombin in blood of man and mammals other than man comprising administering a therapeutically effective amount of a compound of the formula (I) according to claim 1.

5. A process for the preparation of compounds of the formula (I) according to claim 1 characterised in that the fragment

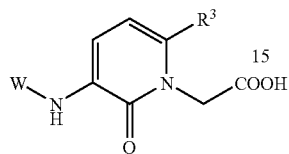

is condensed with the fragment A-B—$NH_2$ by using reagents for the peptide bond formation, wherein $R^3$, W, A and B have the same meaning as in claim 1.

* * * * *